US006087341A

United States Patent [19]
Khavari et al.

[11] Patent Number: 6,087,341
[45] Date of Patent: Jul. 11, 2000

[54] INTRODUCTION OF NUCLEIC ACID INTO SKIN CELLS BY TOPICAL APPLICATION

[75] Inventors: Paul Khavari, Menlo Park; Hongran Fan, Mountain View, both of Calif.

[73] Assignee: The Board of Trustees of the Leland Standford Junior University, Palo Alto, Calif.

[21] Appl. No.: 09/022,584

[22] Filed: Feb. 12, 1998

[51] Int. Cl.[7] .................................................. A61K 48/00
[52] U.S. Cl. ........................................... 514/44; 514/885
[58] Field of Search ............................. 435/455; 514/44, 514/885

[56] References Cited

U.S. PATENT DOCUMENTS

| | | | |
|---|---|---|---|
| 5,160,328 | 11/1992 | Cartmell et al. | 604/307 |
| 5,230,896 | 7/1993 | Yeh et al. | 424/443 |
| 5,254,346 | 10/1993 | Tucker et al. | 424/449 |
| 5,260,896 | 11/1993 | Iwasaki | 364/724.19 |
| 5,580,547 | 12/1996 | Gilchrest et al. | 424/59 |
| 5,589,466 | 12/1996 | Felgner et al. | 514/44 |
| 5,667,798 | 9/1997 | Royds et al. | 424/449 |
| 5,679,647 | 10/1997 | Carson et al. | 514/44 |
| 5,714,162 | 2/1998 | Muller | 424/448 |
| 5,804,566 | 9/1998 | Carson et al. | 514/44 |
| 5,830,877 | 11/1998 | Carson et al. | 514/44 |

FOREIGN PATENT DOCUMENTS

WO 96/18390  6/1996  WIPO.

OTHER PUBLICATIONS

Tang, et al., "Vaccination Onto Bare Skin," *Nature* 388:729–730 (Aug. 21, 1997).
Fenjves et al., "Keratinocyte gene therapy for adenosine deaminase deficiency: a model approach for inherited metabolic disorders" *Hum Gene Ther* (1997) 8(8):911–917.
Garlick et al., "Karetinocyte gene transfer and gene therapy" *Crit Rev Oral Biol Med* (1996) 7(3):204–221.
Fenjves, "Approaches to gene transfer in keratinocytes" *J Invest Dermatol* (1994) 103(5 suppl): 70S–75S.
Fenjves et al., "Systemic distribution of apolipoprotein E secreted by grafts of epidermal keratinocytes: implications for epidermal function and gene therapy" *Proc Natl Acad Sci USA* (1989) 86(22):8803–8807.
Fenjves et al., "Systemic delivery of secreted protein by grafts of epidermal keratinocytes: prospects for kearinocyte gene therapy" *Hum Gene Ther* (1994) 5(10):1241–1248.
Eming et al., "Gene therapy for tissue repair: approaches and prospects" *Br J Plast Surg* (1997) 50(7):491–500.
Moelling, "DNA for genetic vaccination and therapy" *Cytokines Cell Mol Ther* (1997) 3(2):127–136.
Choate et al., "Transglutaminase 1 delivery to lamellar ichthyosis keratinocytes" *Hum Gene Ther* (1996) 7(18):2247–2253.
Gerrard et al., "Recombinant factor IX secreted by transduced human keratinocytes is biologically active" *Br J Haematol* (1996) 95(3):561–563.

Zhang et al., "Depth–targeted efficient gene delivery and expression in the skin by pulsed electric fields: an approach to gene therapy of skin aging and other diseases" *Biochem Biophys Res Commun* (1996) 220(3):633–636.
Vogel et al., "Gene therapy for skin diseases" *Adv Dermatol* (1996) 11:383–398.
Slama et al., "Gene transfer" *Ann Plast Surg* (1995) 35(4):429–439.
Lu et al., "Stage I clinical trial of gene therapy for hemophilia B" *Sci China B* (1993) 36(11):1342–1351.
Sun et al., "Transfection with a aFGF cDNA improves wound healing" *J Invest Dermatol* (1997) 108(3):313–318.
Giachetti et al., "Increased oligonucleotide permeability in keratinocytes of artificial skin correlates with differentiation and altered membrane function" *J Invest Dermatol* (1996) 107(2):256–262.
Rios et al., "Adenovirus–mediated gene transfer to normal and atherosclerostic arteries. A novel approach." *Arterioscler Thromb Vasc Biol* (1995) 15(12):2241–2245.
Li et al., "Topical liposome delivery of molecules to hair follicles in mice" *J Dermatol Sci* (1997) 14(2):101–108.
McDonnell et al., "Immunization," *JAMA* (1997) 278(22):2000–2007.
Walker, "American Academy of Dermatology 1997 Awards for Young Investigators in Dermatology. Direct targeting of skin with DNA vaccines for genetic immunization agains Leishmania in a murine model" *J Am Acad Dermatol* (1997) 37(5 Pt 1):776–777.
Barnes et al., "Asparagine–linked glycosylation in *Saccharomyces cerevisiae*: genetic analysis of an early step" *Mol and Cell Biol* (1984) 4(11):2381–2388.
Robinson et al., "DNA vaccines" *Seminars in Immunology* (1997) 9:271–283.
Barry et al., "Biological features of genetic immunization" *Vaccine* (1997) 15(8):788–791.
Feltquate et al., "Different T helper cell types and antibody isotypes generated by saline and gene gun DNA immunization" *Journal of Immunology* (1997) 158:2278–2284.
Yokoyama et al., "DNA immunization: effects of vehicle and route of administration on the induction of protective antiviral immunity" *FEMS Immunology and Medical Microbiology* (1996) 14:221–230.

(List continued on next page.)

*Primary Examiner*—Bruce R. Campell
*Assistant Examiner*—Richard Shnizer
*Attorney, Agent, or Firm*—Jonathan Alan Quine; Stacy Landry; The Law Offices of Jonathan Alan Quine

[57] ABSTRACT

Skin cells are genetically altered to express a gene product encoded by an introduced polynucleotide. Specifically, the invention involves introduction of a nucleotide of interest into a skin cell by topical application of a polynucleotide that is substantially free of liposomes or charged lipids, where the skin can be either treated or untreated prior to application. Similarly, the invention involves introduction of a nucleotide of interest into a skin cell by topical application of a polynucleotide formulation comprising a liposome or charged lipid, wherein the skin is not treated by removal of hair prior to application. The method of the invention serves as a platform for delivering polynucleotides to skin cells for expression therein for any of a variety uses including, but not limited to genetic immunization.

15 Claims, 3 Drawing Sheets

OTHER PUBLICATIONS

Sundaram et al., "Particle–mediated delivery of recombinant expression vectors to rabbit skin induces high–titered polyclonal antisera (and circumvents purification of a protein immunogen)" *Nucleic Acids Research* (1996) 24(7):1375–1377.

Furth et al., "Gene transfer by jet injection into differentiated tissues of living animals and in organ culture" *Molecular Biology* (1995) 4(2):121–127.

Vahlsing et al., "Immunization with plasmid DNA using a pneumatic gun" *J Immunol Meth* (1994) 175:11–22.

Raz et al., "Intradermal gene immunization: the possible role of DNA uptake in the induction of cellular immunity to viruses" *Proc Natl Acad Sci USA* (1994) 91:9519–9523.

Johnston et al., "Gene gun transfection of animal cells and genetic immunization" *Methods in Cell Biology* (1994) 43:353–365.

Lu et al., "Topical application of viral vectors for epidermal gene transfer" *Journal of Investigative Dermatology* (1997) 108(5):803–808.

INTRODUCTION OF NUCLEIC ACID INTO SKIN CELLS BY TOPICAL APPLICATION

FIELD OF THE INVENTION

The present invention relates generally to in vivo introduction of a polynucleotide into a cell of a vertebrate to accomplish expression of the encoded gene product. Specifically, the invention relates to methods and compositions for in vivo genetic alteration of skin cells by topical application of a polynucleotide of interest.

BACKGROUND OF THE INVENTION

Skin is a versatile organ that serves as a self-renewing and self-repairing interface between the body of a vertebrate organism and its environment. The skin covers the entire external surface of the body. In humans this includes the external auditory meatus, the lateral aspect of the tympanic membrane, and the vestibule of the nose. The skin is continuous with, but distinct from, the mucosae of the alimentary, respiratory, and urogenital tracts; the specialized skin of the mucocutaneous junctions connects the skin and the mucosae. In addition to its protective functions, skin is capable of absorption, and excretion, and is also an important primary site of immunosurveillance against the entry of antigens and initiation of the primary immune response. Skin also performs many biochemical synthetic processes that have both local and systemic effects, and in this sense can be regarded as an endocrine organ. For example, skin is responsible for the formation of vitamin D, and also synthesizes cytokines and growth factors. For a detailed review of skin and its functions, see *Gray's Anatomy: The Anatomical Basis of Medicine and Surgery*, Williams et al. (eds.) 1995 Churchill Livingstone, New York, pgs. 376–417.

Skin can be divided into two major classes: thin, hairy (hirsute) skin (which covers most of the body), and thick, hairless (glabrous) skin (which forms the surfaces of the palms of the hands, soles of the fee, and flexor surfaces of the digits). Both classes of skin are composed of three basic layers: the epidermis, the dermis, and the hypodermis. The primary differences in the two classes of skin are in thickness of their epidermal and dermal components, and in the presence of hairs with their attendant sebaceous glands and arrector pili muscles (pilasebaceous units).

The epidermis, a stratified keratinous squamous epithelium primarily composed of keratinocytes, can be further divided into several strata (from deep to superficial): stratum basale, stratum spinosum, stratum granulosum, stratum lucidum (where present), and stratum corneum. Epidermal appendages (e.g., pilosebaceous units, sudoriferous gland, and nails) are formed by ingrowth or other modification of the general epidermis, often referred to as the interfollicular epidermis. In addition to keratinocytes, the mature epidermis also contains nonkeratinocytes including melanocytes (pigment-forming cells), Langerhans cells (which are immunocompetent antigen-presenting cells derived form bone marrow), and lymphocytes. The epidermis also include Merkel cells, which are thought to be modified keratinocytes.

The population of keratinocytes undergoes continuous renewal, with a mitotic layer of cells at the base of the epidermis replacing those shed at the surface. In order to maintain a constant thickness, the rate of cell production must equal the rate of cell loss. Thus at any one time in the basal layer of the epidermis there are a variety of keratinocytes in different states of differentiation. These keratinocytes can be classified into three types according to their clonal proliferative capacity: 1) stem cells, which have extensive growth capacity; 2) differentiated paraclones, which have limited growth capacity; and 3) intermediate meroclones, which are thought to constitute long-lived progenitor cells (Trainer et al. 1997 *Hum. Mol. Genet.* 6:1761–7; Barrandon et al. 1987 *Proc. Natl. Acad. Sci. USA* 84:2302–6).

The cellular system responsible for both local and systemic humoral and cellular immune responses mediated in the skin is referred to as the skin-associated lymphoid tissue (SALT). SALT primarily comprises Langerhans cells, T cells, and keratinocytes of the epidermis, as well as fibroblasts, macrophages, mast cells, eosinophils, neutrophils, Langerhans cells, T-cells and B cells (including plasmacytes) of the dermis. The Langerhans cell, a key SALT element, belongs to the general group of dendritic cells (DC), mononuclear phagocytic cells important in immunological reactions. Langerhans cells carry receptors for the Fc portion of IgG and for complement components (C3b–C4b and C4d), and express a variety of antigens, including MHC Class I and Class II. Langerhans cells internalize and process antigen, and migrate to the draining lymph nodes to present the antigen to T cells, resulting in T cell activation and proliferation, and generation of cytotoxic T-cells. The keratinocyte, which expresses Ia antigen, produces cytokines that can enhance or downregulate T-cell activation.

The skin, particularly the epidermis, is appealing as a target tissue for delivery of polynucleotides. First, as indicated above, skin mediates a variety of important local and systemic functions, including development of immunity, and expression of polypeptides for local and systemic delivery. These normal skin cell functions can be exploited to mediate expression of a desired recombinant polynucleotide, and to elicit the desired immunological and/or physiological phenomenon. For example, skin has been successfully used as a site for genetic immunization (i.e., immunization by administration of an antigen-encoding sequence) (see, e.g., U.S. Pat. No. 5,589,466; Robinson et al. 1997 *Sem Immunol* 9:217–83; Johnston et al. 1994 *Meth Cell Biol* 43:353–65; Barry et al. 1997 *Vaccine* 15:788–91; Sundaram et al. 1996 *Nucl. Acids Res.* 24:1375–7; Moelling 1997 *Cytokines Cell Mol. Ther.* 3:127–35). Second, skin is an attractive target organ due to its accessibility, thereby providing one of the easiest routes of administration. Moreover, because it is a stratified epithelium, skin allows for the possibility of targeting gene expression to either differentiated or proliferative cells, depending upon the desired effect of gene product expression. In addition, epidermal biology is relatively well-characterized at both the cellular and molecular levels. For example, the regulatory sequences of the keratins have been used to express a variety of exogenous genes in the epidermis of transgenic mice, and are readily adaptable for expression in other organisms (Greenhalgh et al. 1994 *J. Invest. Dermatol.* 103:63S–69S; Vassar et al. 1991 *Genes Dev* 5:714–27; Bailleul et al. 1990 *Cell* 62:697–708).

Expression of a recombinant gene product in skin could also be used in the therapy of a wide variety of diseases including acquired or genetic diseases of the epidermis, as well as conditions amenable to treatment by delivery of gene products systemically. Since the epidermis is know to secrete a variety of cytokines (Luger 1990 *J. Invest. Dermatol.* 95: 100S–104S) and growth factors (Pittelkow et al. 1988 *Am NY Acad Sci* 548:211–24), the skin could be exploited as a bioreactor designed for the secretion of gene products that have a local or a systemic effect (e.g., factor IX, hGH, etc). For example, the skin could be used as a site of metabolic waste disposal for circulating toxins such as oxyadenosine, the toxin of ADA deficiency (Blaese 1992 *Pediatric Res* 33(suppl):S49–S55; Flowers et al. 1990 *Proc Natl Acad Sci. USE* 87:2349–53). For reviews on the use of skin as a target for gene product delivery, see Trainer et al. 1997 *Hum Mol Genet* 6:1761–7; Greenhalgh et al. 1994 *J. Invest Dermatol* 103:63S–69S; Khavari et al. 1997 *Dermatol Clin* 15:27–35).

Conventional methods for delivery of polynucleotides for expression in the skin include invasive, semi-invasive, or non-invasive methods. Invasive methods involve breaking the skin or otherwise disrupting or bypassing the epidermal barrier. Conventional invasive methods include needle injection (U.S. Pat. No. 5,589,466; Masayuki et al. 1996 *FEMS Immunol Med Microbiol* 14:221–30; Ciernik et al. 1996 *Hum Gene Ther* 7:893–9), particle bombardment ("gene gun;" Vahlsing et al. 1994 *J. Immunol Meth* 175:11–22; Cheng et al. 1993 *Proc. Natl. Acad. Sci. USA* 90:4455–9; Sundaram et al. 1996 *Nucl. Acids Res.* 24:1375–7; Johnston et al. 1994 *Meth Cell Biol* 43:353–65), and jet injection (Furth et al. 1995 *Molec Biotech* 4:121–7). Expression of an exogenous DNA has also been accomplished by direct application of DNA or DNA-liposome complexes to incisional wounds (Sun et al. 1997 *J Invest Dermatol* 108:313–8). Semi-invasive methods involve permeabilization of the epithelium through either mechanical or chemical means. For example, one successful semi-invasive method involves the application of a pulsed electric field to the skin (Zhang et al. 1996 *Biochem Biophys Res Commun* 220:633–6). The invasive and semi-invasive methods generally deliver the polynucleotide in the form of naked DNA (see, e.g., U.S. Pat. No. 5,589,466). Non-invasive methods include topical application of a DNA-containing formulation that contains transfection-facilitating molecules. Examples of such formulations include liposomes (Li et al. 1995 *Nature Med* 1:705–6; Alexander et al. 1995 *Human Mol Genet* 4:2279–85). In general, conventional non-invasive methods involve pretreatment of the skin to remove hair (e.g., by shaving and/or use of a depilatory) (Li et al. 1995 *Nature Med* 1:705–6; Alexander et al. 1995 *Human Mol Genet* 4:2279–85).

Although conventional methods hold great promise for delivery of gene products to the skin of local and systemic effects, the more complicated the delivery method or the delivery formulation, the more difficult application of these methods and formulations will be in the field. For example, a genetic vaccine preferred for use in the field would be one that requires no special equipment, such as instruments for breaking the skin to deliver the DNA, and further involves no special formulation that might require special handling. Methods that use needles or require multiple dosages via an invasive route meet with problems of patient compliance. Finally, it would be desirable to have a means to avoid the use of recombinant viruses, which may have undesirable side effects and safety concerns.

There is a need in the field for methods of delivery of polynucleotides to skin cells that does not require special formulations or invasive procedures to facilitate delivery of the genetic material into skin cells. The present invention addresses this problem.

SUMMARY OF THE INVENTION

Skin cells are genetically altered to express a gene product encoded by an introduced polynucleotide. Specifically, the invention involves introduction of a nucleotide of interest into a skin cell by topical application of a polynucleotide that is substantially free of liposomes or charged lipids, where the skin can be either treated or untreated prior to application. Similarly, the invention involves introduction of a nucleotide of interest into a skin cell by topical application of a polynucleotide formulation comprising a liposome or charged lipid, wherein the skin is not treated by removal of hair prior to application. The method of the invention serves as a platform for delivering polynucleotides to skin cells for expression therein for any of a variety uses including, but not limited to genetic immunization.

In one aspect, the invention features a method for inducing an immune response in a vertebrate by applying topically to the skin of a subject an immunogen-encoding polynucleotide in an amount sufficient for uptake by a skin cell and sufficient for expression of the immunogen-encoding polynucleotide to induce an immune response, wherein the polynucleotide is substantially free of liposomes or charged lipids. Preferably the polynucleotide is not contained within a viral particle, and the skin to which the polynucleotide is applied is intact and is not pretreated to remove hair.

In another aspect, the invention features a method for introducing a polynucleotide into a skin cell in vivo for expression of a gene product encoded by the introduced polynucleotide by applying topically to skin of a subject a polynucleotide in an amount sufficient for uptake by a skin cell and sufficient for expression of a gene product encoded by the polynucleotide to provide in the subject a biological effect associated with gene product expression, wherein the polynucleotide is not contained within a viral particle and is substantially free of liposomes or charged lipids.

In another aspect, the invention features a method for producing a non-human transgenic mammal by applying topically to skin of a non-human mammal a transgenic polynucleotide in an amount sufficient for uptake by a skin cell and transformation of the skin cell with the transgenic polynucleotide, wherein the polynucleotide is substantially free of liposomes or charged lipids. In a related aspect the invention features a non-human transgenic mammal produced according to this method, which transgenic mammal is characterized by expression of the transgenic polynucleotide primarily in skin cells of the mammal.

In still another aspect, the invention features a method for delivering a polypeptide to a subject by applying topically to skin of the subject a polypeptide-encoding polynucleotide in an amount sufficient for uptake by a skin cell and sufficient for expression of the polypeptide to provide in the subject a biological effect associated with polypeptide expression, wherein the polynucleotide is not contained within a viral particle and is substantially free of liposomes or charged lipids.

A primary object is to provide a non-invasive method of delivery of genetic material into a skin cell for expression of a gene product encoded by the introduced nucleic acid.

Another object is to produce genetically transformed skin cells, which cells have episomally or genomically incorporated the introduced polynucleotide which, when expressed, produces a biologically active polypeptide (e.g., a polypeptide that elicits a humoral or cellular immune response, exhibits an enzymatic activity, plays a desired structural role in the cell, stimulates a desired physiological response, etc.).

An advantage of the present invention is that the method allows for genetic alteration of skin cells without the need for pretreatment of the skin (e.g., to remove hair or increase skin permeability) or the use of special, transfection-facilitating formulations (e.g., liposomal formulations or recombinant viruses).

Still another advantage of the invention is that it provides a method for genetic immunization that is uncomplicated, requires no special equipment, and is non-toxic.

Another advantage of the invention is that it allows for delivery of a wide diversity of gene product in a single preparation and administration, including but not limited to multiple antigenic variants of a specific pathogen and multiple interacting biologically active proteins.

These and other objects, advantages and features of the present invention will become apparent to those persons skilled in the art upon reading the details of the methodology and compositions as more fully set forth below.

BRIEF DESCRIPTION OF THE DRAWING

FIG. 4B), and laminin 5 (FIG. 4C). In FIG. 4A, lane 1: control anti-β-galactosidase antibody; lane 2: preimmune serum; lane 3: immune serum. I, II, III, IV, and V indicate the position of β-galactosidase (I) and its degradation products. In FIG. 4B, lane 1: immune serum; lane 2: preimmune serum; lane 3: positive control (mouse anti-GFP antibody). In FIG. 4C, lane 1: immune serum; lane 2: preimmune serum; lane 3: positive control (mouse anti-laminin 5 β3 subunit).

FIG. 5A: lanes 1 and 4: 1 μg; lanes 2 and 5: 0.1 μg; lanes 3 and 6: 0.01 μg of β-galactosidase; lanes 1, 2 and 3 were the positive control; lanes 4, 5, and 6 were with the immune serum. FIG. 5B: lane 1: 10 μg; lane 2: 1 μg; lane 3: 0.1 μg; and lane 4: 0.01 μg of β-galactosidase.

DESCRIPTION OF THE PREFERRED EMBODIMENTS

Figure 1:
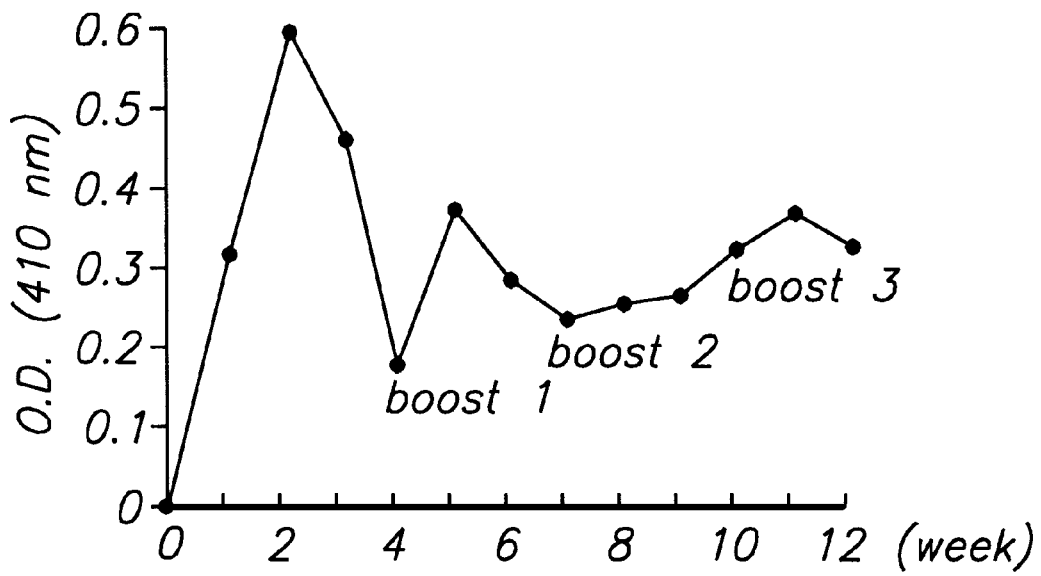
FIG. 1 is a graph showing a time course of IgM production in mice after topical application of β-galactosidase-encoding DNA.

Before the present method of the invention is described, it is to be understood that this invention is not limited to the particular methodology, protocols, skin cell types, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a skin cell" includes a plurality of such cells and reference to "the construct" includes reference to one or more constructs and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cells, constructs, and methodologies that are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

Definitions

By "skin" is meant the tissue of the organ that forms the external surface of the vertebrate body (in humans and like mammals this includes the external surfaces of the external auditory meatus, the lateral aspect of the tympanic membrane, and the vestibule of the nose). Skin is continuous with, but distinct from, the mucosae of the alimentary, respiratory, and urogenital tracts. "Skin" as used herein can also include the specialized skin of the mucocutaneous junctions that connect the skin and the mucosae. "Skin" as used herein includes both thin, hairy (hirsute) skin and thick, hairless (glabrous) skin; preferably, the skin referred to herein is the hirsute skin. Unless specifically stated otherwise, "skin" is meant to include cells either permanently or transiently located within the epidermis, the dermis, and the hypodermis.

"Skin cell" as used herein is meant to encompass cells permanently (i.e., for the majority of the cell's lifespan) or transiently present within skin (e.g., within the epidermis, dermis, or hypodermis). "Skin cells" include, but are not necessarily limited to, keratinocytes, melanocytes, Langerhans cells, cells of hair follicles (e.g., cells of the sebaceous glands, arrector pili muscle, and other members of the pilosebaceous units), cells of sudoriferous glands, Merkel cells, stem cells (e.g., the progenitors of mature keratinocytes), fibroblasts, and lymphocytes (e.g., T cells, B cells (including plasmacytes), macrophages, mast cells, eosinophils, neutrophils, and other cells of the SALT).

By "naked polynucleotide" or "naked DNA" or "naked nucleic acid" and the like is meant a nucleic acid molecule that is substantially free of liposomes and charged lipids (e.g., Lipofectin™). Preferably, "naked polynucleotides" are not contained within a viral particle, and further is substantially free of other transfection-facilitating molecules such as viral polypeptides, detergents (e.g., polybrene), and DEAE-dextran.

By "substantially free" of a transfection-facilitating molecule (e.g., as in "substantially free of liposomes or charged lipids") is meant that the polynucleotide is not associated with an amount of the recited transfection-facilitating molecule that would be significant in effecting delivery of the polynucleotide into the skin cell.

By "polynucleotide of interest" is meant any DNA or RNA molecule that encodes a polypeptide or other gene product that is desirable for expression in a skin cell of a subject, which gene product can include a polypeptide (e.g., an immunogenic polypeptide), an anti-sense mRNA, or other gene product that is desirably expressed by a skin cell. The term "DNA of interest" or "DNA" is used herein as shorthand to refer to the polynucleotide of interest and is not meant to be limiting.

By "construct" is meant a recombinant nucleic acid molecule that contains the polynucleotide of interest (e.g., the DNA of interest). In general, the polynucleotide of interest is operably linked to a promoter for expression of the encoded gene product. Normally, "construct" is generally meant to refer a nucleic acid molecule that facilitates expression of a gene product encoded by the polynucleotide to be introduced into a skin cell.

The phrase "topical administration" is used in its conventional sense to mean delivery of an agent to the skin. In general, such topical administration does not require breaking (or additional breakage) of the skin by, for example, use of a needle or abrasion. Although such administration does not require breakage of the skin to accomplish drug delivery, "topical administration" as used herein is meant to encompass administration to intact skin as well as to skin that has been broken prior to topical administration (e.g., as in delivery to a wound).

By "topical vehicle" or "topical carrier" is meant a vehicle suitable for topical application of a drug, and includes any such materials known in the art, e.g., any liquid or nonliquid carrier, gel, cream, ointment, lotion, paste, emulsifier, solvent, liquid diluent, powder, or the like, which is stable with respect to all components of the topical pharmaceutical formulation.

By "immunogen" is mean an antigenic polypeptide that, when expressed in a vertebrate, elicits an immune response, particularly a protective immune response (e.g., an immune response that provides for protection against infection with the infectious agent from which the antigenic polypeptide is derived).

By "immunity-conferring polypeptide" is meant those polypeptides that comprise an epitope that upon exposure to the immune system of a vertebrate (generally, a mammal), either alone or in the presence of a molecule that facilitates immune response induction (e.g., a carrier molecule or an adjuvant), can act as an endogenous immunogen to provoke or modulate a humoral immune response, a cellular immune response, or both.

"Immune response" is meant to encompass both humoral (antibody) and cellular (e.g., cytotoxic T cell) responses of the immune system, as well as yet unidentified mechanisms of development of immunity.

By "operably linked" is meant that a DNA sequence and a regulatory sequence(s) (e.g., a promoter sequence) are connected in such a way as to permit transcription when the appropriate molecules (e.g., transcriptional activator proteins) are bound to the regulatory sequence(s).

By "subject" is meant any vertebrate to which delivery of the polynucleotide of interest is desired. By "mammalian subject" is meant any mammal to which delivery of a DNA of interest is desired, including human, bovine, equine, canine, and feline subjects.

Overview of the Invention

The present invention is based on the discovery that skin cells can be genetically altered by topical application of a polynucleotide. The polynucleotide can be introduced into cells without any pretreatment of the skin (e.g., to remove hair, to render the skin more permeable (e.g., by administration of a chemical agent or using mechanical means (e.g., abrasion)), or to elicit a non-specific immune response at the site of administration (e.g., by application of a chemical irritant or by application of mechanical means)). Furthermore, delivery of the polynucleotide into skin cells does not require any special formulations, i.e., the polynucleotide can be formulated with substantially no transfection-facilitating molecules such as liposomes or charged lipids, or viral polypeptides. Moreover, the method of the invention does not require the application of electric pulses, e.g., as in iontophoresis, in order to accomplish polynucleotide delivery to skin cells. In short, polynucleotides can be introduced into skin cells by: 1) topical application of naked DNA (either with or without pretreatment of the skin); or 2) topical application of DNA in a liposome without pretreatment of the skin.

Accordingly, the present invention features methods for introducing a polynucleotide into a skin cell by topical application of the polynucleotide to skin. Topical delivery of the polynucleotide according to the method of the invention can utilize, but does not require transfection-facilitating molecules such as liposomes or charged lipids. Moreover, the method of the invention does not require, but can involve, pretreatment of the skin (e.g., to remove hair or to render the skin more permeable). The method of the invention thus provides for genetic alteration of skin cells without the need for invasive procedures (e.g., injection, particle bombardment, or jet injection), without the need for pretreatment of the skin (e.g., shaving or other means of hair removal (e.g., depilatories), permeability enhancers, etc.), and without the need to formulate the polynucleotide with molecules that can act to facilitate entry of the polynucleotide into the cell (e.g., liposomes or liposomal formulations, charged lipids (e.g., Lipofectin™, viral polypeptides, or DNA-protein complexes).

The method of the invention can thus be exploited as a platform for polynucleotide delivery and thus is useful in a variety of applications. Of primary interest is the delivery of a polynucleotide to accomplish genetic immunization. Genetic immunization involves delivery of a polynucleotide to cells for expression of the encoded immunogen within the target tissue. An immune response against the immunogen is mounted in the animal, resulting in development of humoral and/or cellular immunity. Without being held to theory, the immune response is most likely facilitated by the Langerhans cells, which present the immunogen expressed by skin cells (which cells may include Langerhans cells themselves) to other cells of the immune system. Preclinical trials with polynucleotide-based immunizations, particular DNA-based immunizations, have had outstanding success. Genetic immunizations have provided protection against viral, bacterial, and parasitic diseases, modulated the effects of autoimmune and allergic disease, and provided a tool for the control of various cancers (for a review, see Robinson et al. 1997 *Sem Immunol* 9:271–83). Topical administration of polynucleotides according to the method of the invention, which results in genetic alteration of skin cells and induction of an immune response (see Examples below), can, like other routes of DNA- or RNA-based genetic immunization, be used to elicit protective immunity.

The method of the invention is also useful in a variety of other settings in which genetic alteration of skin cells is desirable. For example, the method of the invention can be used to generate transgenic animals, which are characterized by expressing the introduced polynucleotide primarily in skin cells. The method of the invention can also be used as to deliver biologically active (e.g., therapeutic or prophylactic) polypeptides to the skin of a subject or to the subject systemically.

The invention will now be described in further detail.

Polynucleotide Materials and Formulations Suitable for Delivery

The polynucleotide materials for delivery to skin cells according to the method of the invention in general comprise a polynucleotide of interest (which encodes a gene product for which expression in the skin cell is desired) and a promoter for expression of the gene product encoded by the polynucleotide of interest. The polynucleotide of interest and the promoter are operably linked to provide a construct for delivery to the skin of the subject. The construct is preferably provided in combination with a pharmaceutically acceptable carrier, in which the construct is substantially solublized or otherwise provided for application to the surface of the skin.

Polynucleotides of Interest

The polynucleotides of interest for delivery into skin cells according to the methods of the invention include DNA and RNA sequences encoding a gene product having a desirable biological activity (e.g., immunogenic, enzymatic, or other biological activity), as well as DNA or RNA sequences that have a desirable biological activity (e.g., anti-sense RNA, DNA coding for tRNA, or rRNA to replace defective or deficient endogenous molecules). The polynucleotide delivered to the skin cells in vivo can take any number of forms. For example, the polynucleotide can be introduced as a linear or circular molecule, preferably a circular molecule (e.g., a circular plasmid or other construct).

The present invention is not limited to any particular polynucleotide coding for any particular polypeptide or other gene product, and the polynucleotide selected will vary with the aim the method is intended to accomplish (e.g., genetic immunization, delivery of a polypeptide for replacement or enhancement therapy, production of transgenic animals as models of a condition or disease, delivery of a gene for gene replacement therapy, etc.). Exemplary gene products that can be expressed in skin cells according to the invention are discussed in more detail below. Plasmids containing genes coding for a large number of physiologically active polypeptides and other gene products, as well as for antigens or immunogens, have been reported in the literature and can be readily obtained by those of skill in the art.

In a preferred embodiment, the polynucleotides of the invention encode a biologically active polypeptide, preferably an immunity-conferring polypeptide (e.g., for genetic immunization) or a therapeutic polypeptide (e.g., for amelioration of a symptom associated with a polypeptide deficiency). A polypeptide is understood to be any translation product of a polynucleotide regardless of size and glycosylation. The gene product can be any gene product that exhibits a desired biological activity (e.g., a functional characteristic (e.g., enzymatic or DNA binding) or structural characteristic (e.g., role in cell architecture or presentation of one or more immunity-conferring epitopes) in the host cell cytoplasm, nucleus, or membrane. Alternatively or in addition, the gene product may exhibit a desired biological activity following expression and secretion from the transformed cell. Immunity-conferring polypeptides include those polypeptides that comprise an epitope that upon exposure to the immune system of a vertebrate (generally, a mammal), either alone or in the presence of a molecule that facilitates immune response induction (known in the immunology art as a carrier molecule), can act as an endogenous immunogen to provoke a humoral immune response, a cellular immune response, or both.

Constructs for Delivery of a Polynucleotide of Interest

Any nucleic acid construct having a eukaryotic promoter operably linked to a DNA of interest can be used in the invention. The constructs containing the DNA sequence (or the corresponding RNA sequence) which may be used in accordance with the invention may be any eukaryotic expression construct containing the polynucleotide sequence of interest. For example, a bacterial plasmid, viral construct (e.g., a construct containing some viral sequences, but substantially free of viral proteins, i.e., not contained within a virus particle), or other DNA construct can be genetically engineered to provide a recombinant DNA molecule having a sequence encoding the desired gene product for delivery to, and expression in, the skin cell. Preferably the construct is capable of replication in both eukaryotic and prokaryotic hosts, which constructs are known in the art and are commercially available. The DNA ultimately applied to the skin according to the method of the invention may be either linear or circular DNA, preferably circular DNA. The polynucleotide, or polynucleotide-containing construct, can be purified according to methods well known in the art and provided in a delivery formulation as described below.

The polynucleotide of interest can be obtained from any of a variety of sources or methods well known in the art (e.g., isolated from suitable cells, produced using synthetic techniques, etc.), and the constructs prepared using recombinant techniques well known in the art. Likewise, techniques for obtaining expression of DNA or RNA sequences in a genetically altered host cell are known in the art (see, for example, Kormal et al., *Proc. Natl. Acad. Sci. USA*, 84:2150–2154, 1987; Sambrook et al. *Molecular Cloning: A Laboratory Manual*, 2nd Ed., 1989, Cold Spring Harbor Laboratory Press, Cold Spring Harbor, N.Y.; each of which are hereby incorporated by reference with respect to methods and compositions for eukaryotic expression of a DNA of interest).

Promoters and Other Construct Elements

Preferably, the DNA construct contains a promoter to facilitate expression of the DNA of interest. The promoter used will vary with the intended aim of the method of the invention. For example, where the method is to be used to accomplish genetic immunization, the promoter is preferably a strong, constitutive eukaryotic promoter such as a promoter from cytomegalovirus (CMV), mouse mammary tumor virus (MMTV), Rous sarcoma virus (RSV), or adenovirus. More specifically, exemplary promoters include the promoter from the immediate early gene of human CMV (Boshart et al., *Cell* 41:521–530, 1985) and the promoter from the long terminal repeat (LTR) of RSV (Gorman et al., *Proc. Natl. Acad. Sci. USA* 79:6777–6781, 1982). Of these two promoters, the CMV promoter is preferred as it provides for higher levels of expression than the RSV promoter.

The selection of the promoter may vary with a variety of other factors including the skin cell type targeted, the nature of the host/subject, the gene product to be expressed, and the desired level of gene product expression. For example, for use in murine systems, suitable strong promoters include RSV LTR, MPSV LTR, SV40 IEP, and metallothionein promoter. In humans, on the other hand, promoters such as CMV IEP may advantageously be used.

Alternatively, the promoter used may be a tissue-specific or cell type-specific promoter. For example, the promoter can be one designed for substantially specific expression within a skin cell or within a specific skin cell type. Exemplary tissue-specific or cell-specific promoters include the keratin promoters (e.g., human keratin 14 promoter (Wang et al. 1997 *Proc Natl Acad Sci US* 94:219–26); bovine cytokeratin gene promoters, BKIII and BKVI (Alexander et al. 1995 *Hum Mol Genet* 4:993–9); keratin 10 gene promoter (Bailleul et al. 1990 *Cell* 62:697–708); and tyrosinase promoters (specific for melanocytes)). Epidermal-specific promoters are reviewed in Fuchs et al. 1994 *Princess Takamatsu Symp* 24:290–302).

The construct can be altered to influence the sustainability of the expression of the polynucleotide of interest in the transformed skin cell. For example, conventional viral vectors fail to sustain expression of the introduced DNA in genetically transformed skin beyond 1 to 4 weeks. For example, expression can be maintained for longer periods (e.g., 10 to 12 weeks) by inactivation of any LTRs present in the construct and introduction of an internal promoter in the construct to drive gene product expression (see, e.g., Deng et al. 1997 *Nature Biotech.* 15:1388–1391).

The constructs of the invention may also include sequences in addition to promoters which enhance transcriptional or translational expression of the encoded gene product. For example, the construct can comprise an internal ribosomal entry site (IRES) to enhance translation of a downstream sequence (see, Murakami et al. 1997 *Gene* 202:23–29). Other components such as a marker (e.g., an antibiotic resistance gene (such as an ampicillin resistance gene) or β-galactosidase) to aid in selection of cells containing and/or expressing the construct, an origin of replication for stable replication of the construct in a bacterial cell (preferably, a high copy number origin of replication), a nuclear localization signal, or other elements that facilitate production of the DNA construct, the protein encoded thereby, or both.

The construct can also contain a polyadenylation sequence, which sequence may be selected from any of a variety of polyadenylation signal sequences known in the art. Preferably, the polyadenylation signal sequence is the SV40 early polyadenylation signal sequence. The construct may also include one or more introns, which can increase levels of expression of the polynucleotide of interest, particularly where the polynucleotide of interest is a cDNA (e.g., contains no introns of the naturally-occurring sequence). Any of a variety of introns known in the art may be used (e.g, the human β-globin intron, which is inserted in the construct at a position 5' to the DNA of interest).

The DNA of interest may be inserted into a construct so that the gene product (e.g., a polypeptide) is expressed as a fusion product (e.g., a fusion protein having β-galactosidase or a portion thereof at the N-terminus and the polypeptide at the C-terminal portion). Production of a fusion protein can facilitate identification of transformed cells expressing the gene product (e.g., by enzyme-linked immunosorbent assay (ELISA) using an antibody which binds to the fusion protein).

The present invention also encompasses the use of DNA coding for a gene product and for a polymerase for transcribing the DNA, and wherein the DNA includes recognition sites for the polymerase. The initial quantity of polymerase is provided by including a polymerase-encoding mRNA in the preparation, which mRNA is translated by the cell. The mRNA preferably is provided with means for retarding its degradation in the cell (e.g., by capping the mRNA, circularizing the mRNA, or chemically blocking the 5' end of the mRNA). One preferred polymerase is phage T7 RNA polymerase and a preferred recognition site is a T7 RNA polymerase promoter.

The polynucleotide sequences useful in the invention may be used in association with other polynucleotide sequences coding for regulatory proteins that control the expression of these polypeptides. The regulatory protein can act by binding to genomic DNA so as to regulate its transcription; alternatively, it can act by binding to messenger RNA to increase or decrease its stability or translation efficiency.

Regulation of expression of the introduced polynucleotide can also be accomplished by incorporating translational regulatory sequences into the construct. In general, translational efficiency has been found to be regulated by specific sequence elements in the 5' non-coding or untranslated region (5' UTR) of the RNA. Positive sequence motifs include the translational initiation consensus sequence (GCC)<A> CCATGG (Kozak 1987 *Nucleic Acids Res.* 15:8125) and the 5<G>7 methyl GpppG cap structure (Drummond et al. 1985 *Nucleic Acids Res.* 13:7375). Negative elements include stable intramolecular 5' UTR stem-loop structures (Muesing et al. 1987 *Cell* 48:691) and AUG sequences or short open reading frames preceded by an appropriate AUG in the 5' UTR (Rao et al. 1988 *Mol. Cell. Biol.* 8:284).

In addition, certain sequence motifs such as the beta globin 5' UTR may act to enhance translation (when placed adjacent to a heterologous 5' UTR). There are also examples of specific 5' UTR sequences which regulate eukaryotic translational efficiency in response to environmental signals. These include the human ferritin 5' UTR (Hentze et al. 1987 *Proc. Natl. Acad. Sci. USA* 84:6730) and the drosophila hsp<7> 5' UTR (Klemenz et al. 1985 *EMBO J* 4:2053). Finally, there are viral 5' UTR sequences which are able to bypass normal cap dependant translation and translational controls and mediate and efficient translation of viral or chimeric mRNAs (Dolph et al. 1988 *J. Virol.* 62:2059), Pelletier et al. 1988 *Nature* 334:320). The construct can include multiple expression cassettes (e.g., two or more expression cassettes, e.g., a first expression cassette comprising a CMV promoter operably linked to an immunogen-encoding polynucleotide, a second expression cassette comprising a promoter (e.g., a CMV promoter) operably linked to a co-stimulating molecule-encoding polynucleotide, etc.). Exemplary constructs useful in the invention are described in, for example, Robinson et al. 1997 *Sem. Immunol.* 9:271–83.

Where the polynucleotide is mRNA, the stability of the polynucleotide must be considered. In general, capping and 3' polyadenylation are the major positive determinants of eukaryotic mRNA stability, and primarily function to protect the 5' and 3' ends of the mRNA from degradation. However, regulatory elements which affect the stability of eukaryotic mRNAs have also been defined, and therefore must be considered in the development of mRNA for delivery. The most notable and clearly defined of these are the uridine rich 3' untranslated region (3' UTR) destabilizer sequences found in many short half-life mRNAs. In addition, specific regulatory sequences that modulate cellular mRNA half life in response to environmental stimuli have also been demonstrated.

Production of the Polynucleotide of Interest

The DNA and/or RNA encoding many of the gene products desirable for expression in skin cells according to the method of the invention have been identified, isolated, and in some instances sequences. The isolated sequences of such gene products have been described in the literature, are available in from public sequence databases such as GenBank, or are otherwise publically available. With the availability of automated nucleic acid synthesis equipment, both DNA and RNA can be synthesized directly when the nucleotide sequence is known or by a combination of PCR cloning and fermentation. Moreover, when the amino acid sequence of a desired polypeptide is known, a suitable coding sequence for the polynucleotide can be inferred.

Where the DNA encoding a gene product of interest has not been isolated, this can be accomplished by various, standard protocols well known to those of skill in the art (see, for example, Sambrook et al., ibid; Suggs et al. 1981 *Proc. Natl. Acad. Sci. USA* 78:6613–6617; U.S. Pat. No. 4,394,443; each of which are incorporated herein by reference with respect to identification and isolation of DNA encoding a gene product of interest). For example, genomic or cDNA clones encoding a specific protein can be isolated from genomic or cDNA libraries using hybridization probes designed on the basis of the nucleotide or amino acid sequences for the desired gene. The probes can be constructed by chemical synthesis or by polymerase chain reaction (PCR) using primers based upon sequence data to amplify DNA fragments from pools or libraries (U.S. Pat. Nos. 4,683,195 and 4,683,202). The clones may be expressed or the DNA of interest can be excised or synthesized for use in other constructs. If desired, the DNA of interest can be sequenced using methods well known in the art.

It may also be desirable to produce altered forms of the gene products of interest (e.g., polypeptides) that have, for example, enhanced or decreased activity relative to the wild-type protein. Methods for production of altered forms of polypeptides or other gene products (e.g., having amino acid substitutions, deletions, and/or additions) are well known in the art.

Polynucleotide Formulations

Polynucleotide sequences delivered according to the method of the invention may be either naked or associated with liposomes or charged lipids (e.g., cationic or anionic lipids). Furthermore, particularly where the polynucleotides are to be delivered to skin that is not pretreated (e.g., skin that has not been shaved or otherwise subjected to hair removal), the polynucleotide sequences can be formulated in liposomes or other lipid-comprising formulation as a delivery vehicle.

Administration of pharmaceutically acceptable salts of the polynucleotides described herein is included within the scope of the invention. Such salts may be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic non-toxic bases include salts of primary, secondary, and tertiary amines, basic amino acids, and the like.

Naked Polynucleotide Formulations

In a preferred embodiment, the polynucleotides delivered are naked. Naked polynucleotides are "naked" in the sense that they are substantially free of transfection-facilitating amounts of liposomes, charged lipids (e.g., Lipofectin™), and cationic polymers (e.g., polylysine). "Naked polynucleotides" are not contained within a viral particle, and further are substantially free of transfection-facilitating amounts of other transfection-facilitating molecules such as viral polypeptides, detergents (e.g., polybrene), and DEAE-dextran. In addition, the naked polynucleotides are substantially free of precipitating agents such as calcium phosphate. The naked polynucleotide formulations may be admixed with an amount of a molecules that is effective as an adjuvant, but where the molecule may facilitate transfection preferably not an amount of molecule that substantially or significantly facilitates transfection. Such adjuvants include, but are not limited to, viral particles (e.g., adenovirus), cationic lipids, or liposomes. An "adjuvant" is a substance that acts as a co-stimulant to enhance or otherwise improve the action of the active compound in eliciting an immune response. As used herein, an amount of a substance that is effective as an adjuvant may be less than an amount of that substance effective to facilitate transfection. Thus, for example, where a lipid is present at an amount effective to act as an adjuvant, the lipid is not necessarily present in an amount effective to facilitate transfection. The adjuvants may be included as a protein or other molecule in the formulation in which the polynucleotide is delivered, or it can be encoded by a polynucleotide that is contained within the same molecule as the polynucleotide of interest, or on a different polynucleotide. For example, the polynucleotide delivered to the subject can comprise a first expression cassette comprising the polynucleotide of interest operably linked to a promoter (e.g., CMV), and a second expression cassette comprising a promoter operably linked to a sequence encoding an adjuvant molecule (e.g., B7.1 protein, see Zhang et al. 1996 *Gene* 183:1–6; He et al. Gene 1996 *Gene* 175:121–5).

Liposome Formulations of Polynucleotides

In another embodiment, particularly when the polynucleotide is to be delivered to untreated skin (e.g., skin that has not been subjected to hair removal), the polynucleotide can be administered as a lipid-comprising formulation (e.g., liposome). To this end, the polynucleotide can be complexed with polycationic substances such as poly-L-lysine or Lipofectin. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. DNA- or RNA-liposome complex formulations comprise a mixture of lipids which bind to genetic material (DNA or RNA) and facilitate delivery of the nucleic acid into the cell. Liposomes which can be used in accordance with the invention include DOPE (dioleyl phosphatidyl ethanol amine), CUDMEDA (N-(5-cholestrum-3-β-ol 3-urethanyl)-N',N+-dimethylethylene diamine). For example, the polynucleotide can be administered in a solution comprising Lipofectin™ (LTI/BRL) at a concentrations ranging from about 2.5% to 15% volume:volume DNA:lipid, preferably about 6% to 12% volume:volume, more preferably about at a ratio of about 1:2 to about 1:5 weight:weight, still more preferably at a ratio of about 1:3 weight:weight. Methods and compositions for formulation of lipid-containing polynucleotides, including methods and compositions for preparation of liposomes are well known in the art.

Carriers and Forms of the Polynucleotide Formulations

The polynucleotide formulations useful in the present invention will generally comprise a pharmaceutically acceptable carrier, e.g., any liquid or nonliquid carrier, gel, cream, ointment, lotion, paste, emulsifier, solvent, liquid diluent, powder, or the like, which is stable with respect to all components of the topical pharmaceutical formulation and which is suitable for topical administration of polynucleotides according to the method of the invention. Such carriers are well known in the art.

A topical carrier, as noted above, is one which is generally suited to topical drug administration and includes any such materials known in the art. The topical carrier is selected so as to provide the composition in the desired form, e.g., as a liquid, lotion, cream, paste, gel, or ointment, and may be comprised of a material of either naturally occurring or synthetic origin. It is essential, clearly, that the selected carrier not adversely affect the polynucleotide or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like. Particularly preferred formulations herein are colorless, odorless ointments, lotions, creams and gels.

Ointments, which are semisolid preparations, are typically based on petrolatum or other petroleum derivatives. As will be appreciated by the ordinarily skilled artisan, the specific ointment base to be used is one that provides for optimum polynucleotide delivery, and, preferably, provides for other desired characteristics as well, e.g., emolliency or the like. As with other carriers or vehicles, an ointment base should be inert, stable, nonirritating and nonsensitizing. As explained in *Remington: The Science and Practice of Pharmacy*, 19th Ed. (Easton, Pa.: Mack Publishing Co., 1995), at pages 1399–1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be had to *Remington: The Science and Practice of Pharmacy* for further information.

Lotions, which are preparations that are to be applied to the skin surface without friction, are typically liquid or semiliquid preparations in which solid particles, including the polynucleotide, are present in a water or alcohol base. Lotions are usually suspensions of solids, and preferably, for the present purpose, comprise a liquid oily emulsion of the oil-in-water type. Lotions are preferred formulations for polynucleotide delivery to large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like.

Creams containing a polynucleotide for delivery according to the method of the invention are viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in *Remington*, supra, is generally a nonionic, anionic, cationic or amphoteric surfactant.

Gel formulations can also be used in connection with the present invention. As will be appreciated by those working in the field of topical drug formulation, gels are semisolid, suspension-type systems. Single-phase gels contain organic macromolecules distributed substantially uniformly throughout the carrier liquid, which is typically aqueous, but also, preferably, contain an alcohol and, optionally, an oil.

The polynucleotide formulations useful in the invention also encompass sprays, that generally provide the polynucleotide in an aqueous solution which can be misted onto the skin for delivery. Such sprays include those formulated to provide for concentration of the polynucleotide solution at the site of administration following delivery, e.g., the spray solution can be primarily composed of alcohol or other like volatile liquid in which the polynucleotide can be dissolved. Upon delivery to the skin, the alcohol carrier evaporates, leaving concentrated polynucleotide at the site of administration.

The polynucleotide formulations useful in the invention can also contain other optional such as opacifiers, antioxidants, gelling agents, thickening agents, stabilizers, and the like. Other agents may also be added, such as antimicrobial agents, antifungal agents, antibiotics and anti-inflammatory agents such as steroids.

The polynucleotide formulations can include other components that, while not necessary for delivery of polynucleotides to the skin, may enhance such delivery. For example, although it is not necessary to the practice of the invention, the polynucleotide formulations may also contain a skin permeation enhancer. Suitable enhancers are well know in the art and include, for example, dimethylsulfoxide (DMSO), dimethyl formamide (DMF), N,N-dimethylacetamide (DMA), decylmethylsulfoxide ($C_{10}$MSO), $C_2$–$C_6$ alkanediols, and the 1-substituted azacycloheptan-2-ones, particularly 1-n-dodecylcyclazacycloheptan-2-one (available under the trademark Azone® from Whitby Research Incorporated, Richmond, Va.), alcohols, and the like. Preferably, the polynucleotides delivered are substantially free of such permeation enhancers.

It is essential that the additional components do not substantially interfere with the integrity or biological activity of the polynucleotide or the formulation in which it is provided, i.e., the additional components do not adversely affect the uptake of the polynucleotide by skin cells or chemically modify the polynucleotide in an undesirable manner.

It will be recognized by those skilled in the art that the optimal quantity and spacing of individual dosages of polynucleotides will be determined by the precise form and components of the polynucleotide formulation to be delivered, the site of administration, the use to which the delivery device is applied (e.g., immunization, treatment of a condition, production of transgenic animals, etc.), and the particular subject to which the polynucleotide formulation is to be delivered, and that such optimums can be determined by conventional techniques. It will also be appreciated by one skilled in the art that the optimal dosing regimen, i.e., the number of doses of polynucleotides, can be ascertained using conventional methods, e.g., course of treatment determination tests. Generally, a dosing regimen will involve administration of the selected polynucleotide formulation at least once daily, and may be one to four times daily or more.

The practice of the present invention will employ, unless otherwise indicated, conventional techniques of drug formulation, particularly topical drug formulation, which are within the skill of the art. Such techniques are fully explained in the literature. See *Remington: The Science and Practice of Pharmacy*, cited supra, as well as Goodman & Gilman's *The Pharmacological Basis of Therapeutics*, 9th Ed. (New York: McGraw-Hill, 1996).

Dosage Forms of the Polynucleotide Formulations

The polynucleotides can be prepared in unit dosage form (e.g., in ampules), or in multidose form. The polynucleotides may be present in such forms as suspensions, solutions, gels, or creams, preferably in an aqueous vehicle (e.g., in a buffered solution). Alternatively, the polynucleotide salt may be in lyophilized form for reconstitution, at the time of delivery, with a suitable vehicle, such as sterile pyrogen-free water or phosphate-buffered saline (PBS). Both liquid as well as lyophilized forms that are to be reconstituted preferably comprise agents, preferably buffers, in amounts necessary to suitably adjust the pH of the solution. Nonionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid, gel, cream, or solid, may contain from 0.1% to 99% of polynucleotide material.

Where the polynucleotide is administered to elicit an immune response, the formulation may additionally contain agents that act as adjuvants or otherwise facilitate an immune response against the immunogen encoded by the polynucleotide.

Delivery Devices

The polynucleotide formulation can administered using and be provided within, a delivery device(e.g., a patch, bandage, etc.) that provides for both maintenance of contact between the skin of the subject and the polynucleotide formulation and substantially uninhibited movement of the polynucleotide into the skin. The delivery device generally does not in and of itself facilitate movement of the polynucleotide contained therein into the skin, but rather primarily acts to ensure that the polynucleotide formulation is in contact with the skin for a time sufficient to allow genetic alteration of skin cells. The delivery device comprises a delivery means, or "reservoir," which is saturated with a formulation that comprises an amount of polynucleotide sufficient to genetic alteration of skin cells to which it is to be delivered and sufficient to elicit the desired biological effect. For example, where the delivery device is to be used to deliver a polynucleotide for genetic immunization of a human, the delivery means of the device preferably contains an amount of polynucleotide ranging from about 10 µg to about 1,000 µg, preferably from about 100 µg to about 500 µg.

Suitable delivery means of the delivery devices of the invention include, but are not limited to, sponges, hydrogels, and absorptive materials (e.g., gauze) that allow for retention of the polynucleotide formulation at the site of polynucleotide administration without substantially interfering with the delivery of polynucleotide to the skin. It is important that, upon contact of the delivery means with the skin, the polynucleotides contained in the delivery means diffuse or otherwise pass from the delivery means into the skin at a rate and in an amount suitable to accomplish the desired effect.

In general, the delivery means has at least two surfaces: a first surface that serves as a skin-contacting surface; and a second surface opposite the skin-contacting surface. Preferably, the second surface is in contact with a liquid-impermeable coating that substantially prevents movement of the polynucleotide out of the delivery means through the second surface (e.g., in a direction away from the first skin-contacting surface). Preferably, the liquid-impermeable coating also decreases the rate of dehydration of the polynucleotide formulation contained in the delivery means. In one embodiment, the first skin-contacting surface of the delivery means is associated with a liquid-impermeable, removable layer (e.g., release liner), which layer is removed just prior to placement of the first surface on the skin of a subject for administration of the polynucleotide.

The delivery device preferably comprises an adhesive means, which can be a polymeric matrix of a pharmaceutically acceptable contact adhesive material, which serves to affix the system to the skin during drug delivery. The adhesive means facilitates retention of the delivery means on the skin at the desired site of administration. Preferably, the adhesive means comprises an adhesive substance that allows for retention of the delivery means at the desired site for a selected amount of time, but additionally allows for easy removal of the delivery means without substantially adversely affecting the skin with which the adhesive substance was in contact.

The adhesive substance used must be biocompatible with the skin of the subject, and must not substantially interfere with the delivery of polynucleotide to the subject. Examples of suitable skin contact adhesive materials include, but are not limited to, polyethylenes, polysiloxanes, polyisobutylenes, polyacrylates, polyurethanes, and the like. The particular polymeric adhesive selected will depend on the particular polynucleotide formulation, vehicle, etc., i.e., the adhesive must be compatible with all components of the polynucleotide formulation.

In one embodiment, the delivery means and skin contact adhesive are present as separate and distinct layers of the delivery device, with the adhesive underlying the delivery means which, in this case, may be either a polymeric matrix as described above, or it may be a liquid or hydrogel reservoir, or may take some other form. In another embodiment, the delivery means is an adhesive bandage. Exemplary delivery devices suitable for use in the invention include, but are not limited to, those devices described in U.S. Pat. No. 5,160,328; U.S. Pat. No. 5,254,346; U.S. Pat. No. 5,714,162; U.S. Pat. No. 5,667,798; U.S. Pat. No. 5,230,896; and U.S. Pat. No. 5,260,066. Methods for preparation of suitable delivery means and other elements associated with the delivery means, such as an adhesive means are well known in the art.

In another embodiment, the polynucleotide formulation of the invention is provided as a patch, wherein the drug composition is contained within, for example, a laminated structure that serves as a drug delivery device to be affixed to the skin. In such a structure, the polynucleotide composition is contained within a delivery means, or "reservoir," which lies beneath an upper backing layer. The laminated structure may contain a single reservoir, or it may contain multiple reservoirs.

The backing layer in the laminates of the patch, which serves as the upper surface of the delivery device, functions as the primary structural element of the laminated structure and provides the device with much of its flexibility. The material selected for the backing material should be selected so that it is substantially impermeable to polynucleotide and, preferably, to other components of the polynucleotide formulation, thus preventing loss of any components through the upper surface of the device, and preferably substantially impeding dehydration of the composition in the reservoir. The backing layer may be either occlusive or nonocclusive, depending on whether it is desired that the skin become hydrated during drug delivery. The backing is preferably made of a sheet or film of a preferably flexible elastomeric material. Examples of polymers that are suitable for the backing layer include polyethylene, polypropylene, polyesters, and the like.

During storage and prior to use, the laminated structure includes a release liner. Immediately prior to use, this layer is removed from the device to expose the skin-contacting surface of the device, which as noted above may be either the reservoir itself or a separate contact adhesive layer, so that the system may be affixed to the skin. The release liner is preferably made of a material that is substantially impermeable to the polynucleotide and other components in the polynucleotide formulation.

Delivery devices suitable for use in the present invention may be fabricated using conventional techniques, known in the art, for example by casting a fluid admixture of adhesive, polynucleotide, and carrier/vehicle onto the backing layer, followed by lamination of the release liner. Similarly, the adhesive mixture may be cast onto the release liner, followed by lamination of the backing layer. Alternatively, the polynucleotide reservoir may be prepared in the absence of polynucleotide formulation or excipient, and then loaded by "soaking" in a drug/vehicle mixture.

As with the topical formulations of the invention, the polynucleotide formulation contained within the delivery means of the delivery devices may contain a number of components. Furthermore, such delivery devices can be used in connection with administration of any of the polynucleotide formulations described herein, e.g., naked polynucleotide formulations, or lipid- or liposome-comprising polynucleotide formulations. Regardless of the specific basic components of the polynucleotide formulation, the polynucleotide formulation will generally dissolved, dispersed or suspended in a suitable pharmaceutically acceptable vehicle, typically an aqueous solution or gel. Other components that may be present include preservatives, stabilizers, and the like.

Packaging of the Polynucleotide Formulations and Delivery Devices

The units dosage ampules, multidose containers, and/or delivery devices (e.g., patches) in which the polynucleotides are packaged prior to use may comprise an hermetically sealed container enclosing an amount of polynucleotide or polynucleotide formulation containing a polynucleotide suitable for a pharmaceutically effective dose thereof, or multiples of an effective dose. The polynucleotide is preferably packaged as a sterile formulation, and the hermetically sealed container is designed to preserve sterility of the formulation until use. Where the polynucleotides are provided in a patch-style delivery device, the patches may be contained in a strip of individually separable packaged patches for ease in dispensing.

The container in which the polynucleotide formulation and/or delivery device is packaged is labeled, and the label bears a notice in the form prescribed by any appropriate governmental agency. For example, where the polynucleotides are to be administered to humans, the package comprises a notice that reflects approval by the Food and Drug Administration under the applicable federal law, of the manufacture, use, or sale of the polynucleotide material therein for human administration. Federal law requires that the use of pharmaceutical agents in the therapy of humans be approved by an agency of the Federal government. Responsibility for enforcement is the responsibility of the Food and Drug Administration, which issues appropriate regulations for securing such approval, detailed in 21 U.S.C. 301–392. Regulation for biologic material, comprising products made from the tissues of animals is provided under 42 U.S.C 262. Similar approval is required by most foreign countries. Regulations vary from country to country, but the individual procedures are well known to those in the art.

Introduction of Polynucleotides into Skin Cells According to the Method of the Invention Application of the Polynucleotide to Skin Administration of the polynucleotide is accomplished by contacting a polynucleotide-comprising formulation (e.g., a buffered salt solution comprising the polynucleotide) with an area of skin for a time sufficient to allow genetic alteration of skin cells. Preferably, the polynucleotide is applied to hirsute skin. The polynucleotide can be applied to skin without substantial pretreatment or with pretreatment, preferably without pretreatment of the skin. "Pretreatment" can generally encompass removal of hair from the skin, increasing skin permeability by mechanical means (e.g., abrasion), increasing skin permeability by application of a chemical agent to the site either before or during polynucleotide administration, and application of an irritant or other like chemical agent to elicit a non-specific immune response or an immune response toward the irritant (e.g., by application of a keratinolytic agent). Administration of the polynucleotide can be accomplished according to the invention without the application of an electric field or electric pulse (e.g., as in iontophoresis), without breaking the skin (e.g., by abrasion or through use of a needle), and without application of pressure to the site of administration (e.g., via jet propulsion, pressurized air, etc.). Furthermore, polynucleotide administration can be accomplished using a polynucleotide formulation that is substantially free of permeabilizing agents, detergents, or other chemical agents that facilitate entry of the polynucleotide into the skin.

Once the polynucleotide-comprising formulation is brought into contact with skin, contact is maintained for a time sufficient to allow movement of the polynucleotide from the formulation into skin and into skin cells. In general, the time of contact between the polynucleotide and the skin will be at least about 1 min to about 1 hr or more, preferably at least about 30 min. Because there is substantially no toxicity associated with contacting the polynucleotide with the skin, the time of contact maintained between the polynucleotide and the skin to which the polynucleotide is to be delivered is limited only by such factors as the ability to keep the polynucleotide in a suitable delivery form (e.g., a time during which the polynucleotide-comprising solution can be prevented from dehydrating) and the ability to physically maintain contact between the polynucleotide and the site of delivery (e.g., maintenance of a patch comprising the polynucleotide(s) on the skin). Therefore, the time of contact of a single dose can be as long as several hours to several days, and may be weeks or more. Furthermore, the time of delivery can be further extended by additional subsequent applications of the polynucleotide to the same or different delivery site on the skin.

Without being held to theory, after the polynucleotide is applied to the skin the introduced polynucleotide is taken up by skin cells, primarily skin cell in the epidermis, and is incorporated into the cell either episomally or via genomic integration. Preferably, the introduced polynucleotide is maintained for the remaining life of the transformed cell, and may or may not be passed on to any daughter cells.

Expression of Introduced Polynucleotides

Expression of the introduced polynucleotide can be short-term (e.g., a few hours to several hours to a few days) or permanent or long-term (e.g., from a week to several weeks to a few months or more). In general, gene product expression from the introduced polynucleotide ranges from a few days (e.g., 1 to 2 days, or 3 to 5 days), to about 1 week, generally about 1 to 4 weeks, up to about 6 weeks, and may be as long as about 10 to 12 weeks or longer. The short-term nature of gene product expression can be due to loss of the introduced polynucleotide (e.g., where the polynucleotide is present as an episomal element), inactivation of the polynucleotide (e.g., due to methylation and/or heterochromatin-induced inactivation), and/or natural maturation and sloughing off of the transformed skin cell.

Where expression times of more than a few week are desired (e.g., about 10 to 12 weeks or longer), and the construct contains long terminal repeats (LTRs), expression of the gene product can be maintained by inactivation of the LTRs and introduction of an internal promoter in the construct to drive gene product expression (see, e.g., Deng et al. 1997 *Nature Biotech.* 15:1388–1391). The desired length of time for gene product expression will vary according to the aim of polynucleotide delivery to the skin. For example, where the polynucleotide is delivered to accomplish genetic immunization, the gene product is expressed for a time sufficient to allow for expression of the gene product (e.g., immunogenic polypeptide) at a level sufficient to elicit an immune response (e.g., cellular and/or humoral immune response).

Percutaneous absorption of topically applied molecules, such as retinoids, can be used to regulate therapeutic genes controlled by inducible promoters. It may also be possible to regulate expression of a polynucleotide of interest by topical application of synthetic ligands that affect transcriptional activation of a promoter operably linked to the polynucleotide (see, e.g., Freiberg et al. 1997 *J. Clin. Invest.* 99:2610–5, describing transcriptional control in keratinocytes and fibroblasts using the hybrid transcription activators GAL4 and VP16, each linked to the FK506 binding protein). Expression of such specialized regulatory proteins in the skin cell can be accomplished by delivering the appropriate regulatory protein-encoding sequence concomitantly with the polynucleotide of interest.

Exemplary Utilities of the Invention

The method of genetic alteration of skin cells can be applied to a variety of uses including, but not limited to, genetic immunization (e.g., a DNA vaccine), production of transgenic animal models of diseases or conditions (e.g., for use in drug screening or testing), and deliver of therapeutic or prophylactic gene products for treatment or alleviation of symptoms of a systemic or skin-specific condition or disease.

Immunization

Of particular interest is the use of the method of the invention to accomplish genetic immunization, e.g., the eliciting of immune responses against specific polypeptides by expression of genes encoding the polypeptides in a subject's own cells. Genetic immunization. simplifies the vaccination conventional vaccination protocol (e.g., there is no need to purify the antigenic polypeptide in a form that maintains the immunogenic and protective epitopes for delivery to the subject). Genetic immunization using naked polynucleotides further avoids the risk of inoculating infectious agents to the subject, as well as the risk of development of undesirable immune responses to bacteria or viruses used to deliver the immunogenic polypeptides. Furthermore, shedding of transformed skin cells during the normal course of maturation provides an inherent safety feature. Still another advantage is that naked polynucleotides are far more heat stable than most conventional polypeptide-based vaccines, thus avoiding the need for refrigeration.

Immunity-conferring polypeptides are those polypeptides that comprise an epitope that upon exposure to the immune system of a vertebrate (generally, a mammal), either alone or in the presence of a molecule that facilitates immune response induction (known in the immunology art as a carrier molecule), can act as an endogenous immunogen to provoke a humoral immune response, a cellular immune response, or both. Immunity-conferring polypeptides suitable for administration according to the method of the invention are well known in the art, as are methods for identifying immunity-conferring polypeptides, and methods for identifying and isolating polynucleotides encoding such immunity-conferring polypeptides. Immunity-conferring polypeptides for protection against viral, bacterial, and parasitic diseases, or for modulation of the effects of autoimmune and allergic disease, or for control of various cancers are known in the art (for a review, see Robinson et al. 1997 *Sem Immunol* 9:271–83). For a general description of immunity-conferring polypeptides used in conventional methods of vaccination see, Wilson et al. (eds.) *Harrison's Principles of Internal Medicine,* 12th ed., 1991, McGraw-Hill, Inc., New York, pgs. 472–8. See also Austen et al. (eds.) *Therapeutic Immunology,* 1996, Blackwell Science, Cambridge, Mass., for a review of cytokines (pgs. 229–279), anti-idiotype-based therapies (pgs. 363–371), immunotherapy of allergic disease (pgs. 372–384), and vaccines and peptide therapy (pgs. 419–27; 441–450).

Exemplary immunity-conferring polypeptides contemplated by the present invention include, but are not limited to, polypeptides of viruses (e.g., viral envelope proteins, glycoproteins, surface antigens, etc.) such as influenza (e.g., influenza hemagglutinin of influenza types A, B, or C), herpes virus (HSV-1, HSV-2, EBV, varicella-zoster (chickenpox), and CMV), measles, mumps, rubella, polio, hepatitis viruses (e.g., hepatitis A, B, and C (e.g., hepatitis B surface antigen)), RSV, papilloma virus, rabies, rotavirus, St. Louis encephalitis, HIV, FeLV, lymphocytic choriomeningitis, western equine encephalitis, and other viruses, particularly those pathogenic to humans and non-human animals, particularly non-human livestock and other domesticated animals.

Exemplary immunity-conferring polypeptides contemplated by the present invention also include, but are not limited to, polypeptides of pathogenic bacteria (e.g., bacterial surface proteins or toxins (e.g., diphtheria toxin, tetanus toxin, and toxins of Staphylococci, Yersiniae (e.g., *Y. pestis*), Shigella spp. (e.g., *S. dysenteriae, S. flexneri, S. boydii,* and *S. sonnei*) enteropathogenic organisms such as Cholera spp, etc.)). Bacteria from which such polypeptides can be derived include, but are not limited to, Neisseria spp. (e.g., *N. meningitidis, N. gonohorroeae*), Mycobacterium spp. (e.g. *M. tuberculosis*), Haemophilus spp. (e.g., *H. influenzae,* especially type b), Bordetella spp. (e.g., *B. pertussis*), Streptococcus spp., (e.g., *S. pneumoniae*, esp. group B strep), Mycoplasma spp. (e.g., *M. pulmonis*), Leishmania spp., Legionella spp., Chlamydia spp., Salmonella spp. (e.g., *S. typhi*), species of enteropathogenic *Escherichia coli* (e.g., EPEC, EIEC, and EHEC), Staphylococci spp. (e.g., *S. aureus*), Yersiniae spp., Shigella spp. etc. Exemplary immunity-conferring polypeptides contemplated by the present invention include, also include but are not limited to, polypeptides of pathogenic parasites, such as Plasmodium spp. (e.g., species associated with malaria such as *P. falciparum*), nematodes, cestodes, schistosomes, Trichomonas spp., Entamoeba spp., Ascaris spp., etc.

Exemplary immunity-conferring polypeptides contemplated by the present invention include, also include but are not limited to, polypeptides of immune modulators such as GM-CSF, cytokines (e.g., interleukins (e.g., IL-1, IL-2, IL-6, IL-8, IL-12) TNF-$\alpha$, TNF-$\gamma$, interferons (e.g., IFN$\alpha$/$\beta$)), and co-stimulatory molecules (e.g., B7.1 and B7.2). In addition, immunity-conferring polypeptides useful in the invention encode antibodies or fragments thereof to which an anti-antibody response is desired, e.g., to provide an anti-idiotype antibody response.

Thus, the method of the invention can be used to elicit immunity against infectious agents, including bacteria, viruses, and parasites, as well as against tumor cells. Since the immune systems of all vertebrates operate similarly, the applications described can be implemented in all vertebrate systems, comprising mammalian and avian species, as well as fish. The immune response elicited may be enhanced by co-administration of either an adjuvant or lymphokines to further stimulate the lymphoid cells, or by co-administration of a polynucleotide encoding such adjuvants or lymphokines.

Vaccination with nucleic acids comprising an antigen-encoding sequence can also provide a way to specifically target the cellular immune response. Cells expressing polypeptides that are secreted will enter the normal antigen processing pathways and produce both a humoral and cytotoxic response. The response to polypeptides that are not secreted is more selective. Non-secreted polypeptides synthesized in cells expressing only class I MHC molecules are expected to produce only a cellular (cytotoxic) immune response. Expression of the same antigen in cells bearing both class I and class II molecules may produce a more vigorous response by stimulating both cytotoxic and helper T cells. Enhancement of the immune response may be accomplished by introducing into the skin cells sequences encoding a full-length polypeptide antigen, as well as a sequences encoding a peptide fragment(s) of the antigen. The larger polypeptide antigen is presented via class I MHC molecules to the cellular immune system while the peptide fragment is presented via class II MHC molecules to stimulate helper T cells. In any case, the method provides a way to stimulate and modulate the immune response in a way which has not previously been possible.

The method of the invention can be modified to further enhance the immunogenicity of antigens. For example, T cell immunization can be augmented by increasing the density of Class I and Class II histocompatibility antigens on the surface of the transfected cells and/or by inducing the transfected cell to release cytokines that promote lymphocyte proliferation. To this end, polynucleotides encoding a cytokine such as an interferon or an interleukin (e.g., IL-1) can be delivered concomitantly with the polynucleotide encoding the desired antigen. or an activation marker, will result in the elimination of these cells.

The method of the invention avoids the complications of conventional subunit vaccines that involve delivery of gly-coprotein antigens. Such antigens are seldom correctly modified in recombinant expression systems generally used to make the antigens. Introducing the gene for a glycoprotein antigen into the subject skin cells insures that the protein product is synthesized, modified and processed in the same species for which pathogen protection is desired. Thus, for example, the expression of a gene for a human viral glycoprotein will contain the correct complement of sugar residues. This is important because it has been demonstrated that a substantial component of the neutralizing antibodies in some viral systems are directed at carbohydrate epitopes.

Any appropriate antigen which is a candidate for an immune response, whether humoral or cellular, can be used in its nucleic acid form in the method of the invention. The host's skin cells are transformed with an antigen-encoding polynucleotide (either DNA or RNA). The choice of the polynucleotide may depend on the duration of expression desired. In some instances, e.g., where the immunogen is highly toxic to cells of the host, a highly transient expression of the immunogenic peptide, as occurs on mRNA transfection or with non-replicating, non-integrating DNA, may be preferred.

The use of DNA or mRNA vaccine therapy can similarly provide a means to provoke an effective cytotoxic T-cell response to weakly antigenic tumors. For example, if a tumor-specific antigen were expressed by mRNA inside a cell in an already processed form, and incorporated directly into the Class I molecules on the cell surface, a cytotoxic T cell response would be elicited. Such an approach can be used to prevent or treat viral infections, particularly latent viral infections, as well as chronic pathogen infections such as, for example, infections associated with pathogens that replicate slowly and spread directly from cell to cell (e.g., slow viruses (e.g. Visna), prions, HIV, malaria, etc.). One can eliminate the infected cells by inducing an cellular response to proteins of the pathogen. Finally, this approach can also be applied to the treatment of malignant disease. Vaccination to mount a cellular immune response to a protein specific to the malignant state, be it an activated oncogene, a fetal antigen The use of DNA/mRNA vaccines could in this way greatly enhance the immunogenicity of certain viral proteins, and cancer-specific antigens, that normally elicit a poor immune response. Genetic vaccination can be used to, for example, induce cytotoxic T cell immunity against poorly immunogenic viral proteins from the Herpes viruses, non-A, non-B hepatitis, and HIV, while avoiding the hazards and difficulties associated with in vitro propagation of these viruses. For cell surface antigens, such as viral coat proteins (e.g., HIV gp120), the antigen would be expressed on the surface of the target cell in the context of the major histocompatibility complex (MHC), which would be expected to result in a more appropriate, vigorous and realistic immune response. It is this factor that results in the more efficacious immune responses frequently observed with attenuated virus vaccines. Delivery of antigens using the method of the invention would be much safer than, for example, use of attenuated viruses, which can result in a low frequency of disease due to inadequate attenuation.

Furthermore, genetic vaccination according to the present invention is also advantageous during the vaccine development phase. One of the difficulties with vaccine development is the requirement to screen different structural variants of the antigen, for the optimal immune response. If the variant is derived from a recombinant source, the protein usually must be expressed and purified before it can be tested for antigenicity—a process that is laborious and time consuming. With in vitro mutagenesis, it is possible to obtain and sequence numerous clones of a given antigen. Screening for antigenicity at the DNA or RNA level using the present method greatly speeds vaccine research and development.

Finally, genetic vaccines are advantageous since the antigen is never exposed directly to serum antibody, but is always produced by the transfected cells following translation of the mRNA. Therefore, anaphylaxis or other undesirable side effects should be minimized. In addition, the incidence of development of allergic reactions in subjects receiving multiple immunizations (boosters) should also be minimized.

The method of genetic vaccination is also advantageous in that it allows for co-expression of two or more immunogen-encoding polynucleotides, and thus allows for development of immunity based on immune responses to two or more antigens. Preferably, the sequences encoding the multiple immunogens are presented within a single construct (Contry et al. 1996 *Gene Ther* 3:67–74). Thus, for example, it is possible to produce enhanced immunity to the target pathogen since the immune system will be allowed to target multiple specific epitope that confer immunity. Furthermore, it may be possible to vaccinate the individual against two or more different pathogens using a single genetic vaccine.

Subjects to which the method of the invention can be applied to accomplish genetic immunization can be any vertebrate for which vaccination is desired. Such subjects include, but are not limited to, humans, non-human domesticated animals (such as livestock (e.g., cattle, swine, horses, sheep, chickens, turkeys, etc.) and pets (e.g., dogs, cats, rats, mice, hamsters, ferrets, etc.). Efficacy of vaccination can be assessed by methods well known in the art, e.g., examination of blood, tissue, or mucosa, for anti-gene product antibodies and/or the presence of a desired cellular immune response.

Polynucleotides can be administered to accomplish immunization either as a pre-exposure prophylactic measure or, in some cases, as a post-exposure prophylaxis. Furthermore, immune response can be boosted by subsequent, additional administration of polynucleotides to the subject ("boosters"). Appropriate times (e.g., ages of subjects, etc.) and conditions for immunization are well known in the art. The amount of polynucleotide delivered to accomplish genetic vaccination will vary with the subject, skin site to which the polynucleotide is administered, and other factors that will be readily appreciated by the ordinarily skilled artisan. In general, the amount of polynucleotide delivered to a human to elicit an immune response will range from about 0.05 $\mu$g/kg to about 50 mg/kg, usually about 0.005 to 5 mg/kg. Subsequent administrations can be used as boosters to further enhance the immune response and to provide for effective vaccination.

Transgenic Animals

The method of the invention can be used to produce animal models of, for example, any of a variety of skin-specific conditions or diseases. In addition, the method of the invention can be used to generate transgenic animals that are models of systemic diseases (e.g., by delivery of a polypeptide to the general circulation (e.g., hormones such as growth factors, cytokines such as interleukins and interferons, etc.). The transgenic animals generated using the method of the invention can be any non-human vertebrate, generally a non-human mammal, such as a rodent (e.g., mouse, rat, guinea pig, rabbit, etc.), canine, feline, equine, bovine, etc. In general, transgenic animals generated according to the invention are characterized by expression of the introduced polynucleotide substantially only in skin cells (i.e., transcription of the introduced polynucleotide is substantially confined to skin cells, rather than throughout the transgenic animal's body as often observed in transgenic animals generated by transformation of embryonic stem cells or other conventional methods).

The transgenic animals of the invention can be generated to provide animal models of various skin conditions. The method of the invention can also be used to test the efficacy of proposed therapies in available animal models of the conditions. Exemplary gene product of interest for expression in transgenic animals produced by the methods of the invention include, but are not limited to, transglutaminase (in an animal model of lamellar ichthyosis), steroid sulphatase (in an animal model of X-linked ichthyosis), growth factors (e.g., insulin-like growth factor, human growth factor, acidic fibroblast growth factor, transforming growth factor $\beta$, etc., for the study of, e.g., wound healing and prevention of scarring, particularly for incisional wounds and burns), factor IX (for the study of hemophilia and potential treatments therefor), and cytokines (e.g., IL-8, IL-2, IL-6, IL-12, TNF-$\alpha$, TNF-$\gamma$, for, e.g., for study in subcutaneous cancer models).

The amount of polynucleotide delivered to generate the desired transgenic animal will vary with a variety of factors that will be readily appreciated by the ordinarily skilled artisan. In general, dosages will generally range from about 0.05 $\mu$g/kg to about 50 mg/kg, usually about 0.005 to 5 mg/kg.

Amelioration of Conditions, Diseases, or Symptoms Thereof

Various conditions, diseases, and/or symptoms thereof are amenable to treatment via the biological effect of a gene product delivered to the subject using the methods of the invention. The specific gene product delivered using the method of the invention will, of course, vary with the condition, disease, or symptom from which the subject desires relief. Exemplary conditions and diseases, as well as their attendant symptoms, that are amenable to treatment by expression of an appropriate gene product in the skin (e.g., subsequent to introduction of DNA encoding the gene product using the method of the invention) include both skin and systemic diseases. These diseases can be grouped into several categories including, but not limited to, single gene congenital skin diseases, multifactorial acquired skin diseases, and systemic diseases (e.g., diseases of inadequate or poorly controlled circulating levels of specific polypeptides).

For example, recessive monogenic skin disease, such as certain types of epidermolysis bullosa and ichthyosis (e.g., lamellar ichthyosis and X-linked ichthyosis) are among the disease of most interest for treatment using the method of the invention since these disorders require only that the corrective gene be expressed in the appropriate location in the skin (i.e., transglutaminase 1 (TGase 1) and the XP gene, respectively). Treatment of dominant disorders, such as epidermolytic hyperkeratosis and epidermolysis bullosa simplex, require both expression of the desired gene in the skin as well as elimination of the trans dominant effects of the expressed mutant proteins. Complex conditions can be treated as they become better understood at the molecular level. For example, symptoms associated with complex conditions such as psoriasis, may be treated by expression or overexpression of factors that downregulate or block the inflammatory cascade in the skin.

The method of the invention can also be used to accomplish expression of any of a wide range of growth factors (e.g., human growth hormone, hematopoietic growth factors, etc.), cytokines (e.g., interferon, interleukins, etc.), and other gene products that are known to have desirable systemic effects in either protein replacement therapies, enhancement of immune system functions, and the like.

Therapeutic polypeptides thus generally include those polypeptides that can compensate for defects or deficiencies in a mammal, or those that act through toxic effects to limit or remove harmful cells from the body. Specific gene products of interest for delivery according to the method of the invention include, but are not limited to, keratin (e.g., for treatment of epidermolysis bullosa simplex and epidermolytic hyperkeratosis, see, e.g., Korge et al. 1996 *J. Mol. Med.* 74:59–70; Bickenbach et al. 1996 *Differentiation* 61:129–39), TGase 1 (Choate et al. 1996 *Nature Med* 2:1263–7; Choate et al. 1996 *Hum Gene Ther* 7:2247–53), the XP gene (Carreau et al. 1995 *Hum Gene Ther* 6:1308–15), steroid sulphatase (STS; Jensen et al. 1993 *Exp Cell Res* 209:392–7), keratin proliferation inhibitors such as TGF-β (for treatment of psoriasis, e.g., through use of keratin promoters for tissue-specific expression, Ramirez et al. 1995 *Proc Natl Acad Sci USA* 92:4783–7), growth factors (e.g., TGF-β and EGF, e.g., to facilitate wound healing, treatment of burns, and reduction of scarring, see, e.g., Andree et al. 1994 *Proc. Natl. Acad. Sci. USA* 91:12188–92; O'Kane et al. 1997 *Int. J. Biochem Cell Biol.* 29:63–78; Sun et al. 1997 *J Invest Dermatol* 108:313–8), factor IX (for treatment of systemic coagulation disorders, e.g., Gerrard et al. 1993 *Nature Genet* 3:180–3; Lu et al. 1993 *SCI CHIN B* 36:1342–51; Gerrard et al. 1996 *Br J Haemotol* 95:561–3); apolipoprotein E (ApoE; for control of cholesterol levels; see, e.g., Fenjves et al. 1989 *Proc Natl Acad Sci USA* 86:8803–7; Fenjves et al. 1994 *Hum Gene Ther* 5:1241–8), adenosine deaminase (ADA; for treatment of ADA deficiency; see, e.g., Fenjves et al. 1997 *Hum Gene Ther* 8:911–7), HSV thymidine kinase "suicide" gene (followed by administration of gancyclovir to facilitate regression of squamous cell carcinomas; see, e.g., O'Malley et al. 1995 *Cancer Res* 55:1080–5; Liu et al. 1995 *Cancer Res* 55:3117–22). For reviews in this area, see, e.g., Trainer et al. 1997 *Hum Mol Genet* 6:1761–7; Greenhalgh et al. 1994 *J Invest Dermatol* 103:63S–69S; Khavari et al. 1997 *Dermatol Clin* 15:27–35.Eming et al. 1997 *Br J Plast Surg* 50:491–500; Vogel et al. 1996 *Adv Dermatol* 11:383–98; and Slama et al. 1995 *Ann Plast Surg* 35:429–39.

Therapeutic gene products of interest also include antibodies, including chimeric antibodies and hybrid antibodies with dual or multiple antigen or epitope specificities, and fragments, such as F(ab)2, Fab', Fab and the like, including hybrid fragments. Also included within the meaning of "antibody" are conjugates of such fragments, and so-called antigen binding proteins (single chain antibodies). For example, a polynucleotide coding for variable regions of an antibody can be introduced into skin cells in accordance with the present invention to enable the subject to produce antibody in situ. The antibody in turn would exert a therapeutic effect, for example, by binding a surface antigen associated with a pathogen. Alternatively, the encoded antibodies can be anti-idiotypic antibodies (antibodies that bind other antibodies). Such anti-idiotypic antibodies could bind endogenous or foreign antibodies in a treated individual, thereby to ameliorate or prevent pathological conditions associated with an immune response, e.g., in the context of an autoimmmune disease.

Regulation of gene product dosage can be accomplished indirectly by varying such factors as the amount of DNA applied to the skin, the area of the site of application, and the frequency of dosage. Since the gene products are expressed for a relatively short period of time (e.g., generally less than about 14 days), the amount of gene product expressed and delivered can be regulated by increasing or decreasing dosage in subsequent applications. Further, if the subject should require higher or lower levels of gene product delivered, the dosage of the DNA can be readily adjusted to provide such. Thus, the short term of gene product expression is advantageous in that it provides greater flexibility to the clinician or veterinarian.

Unlike genetic-based therapies proposed in the past, one major advantage of the present invention is the transitory, short-term nature of the polynucleotide synthesis in the cells. For most applications, the genetic alteration in the skin of the subject is preferably not permanent, e.g., due to the presence of the introduced nucleotide as an episomal element rather than as a genomically-integrated element and/or the shedding or other turn-over of the transformed cells. Thus, the method of the invention accomplishes expression of a desired gene product in the subject without serious concern of any substantial genetic liability. For example, where it is desirable to provide for transient or short-term gene product expression, the polynucleotide can be designed so that it is non-replicating or incapable of genomic integration.

Assessment of Efficacy of the Method of the Invention

The effects of expression of the gene product encoded by the polynucleotide of interest following in vivo transfer can be monitored in a variety of ways. Generally, a sample of blood or tissue from the subject can be assayed for the presence of the encoded gene product. Appropriate assays for detecting a gene product of interest (e.g., a polypeptide) in blood, plasma, or tissue samples are well known in the art. For example, a sample of blood can be tested for the presence of the polypeptide using an antibody that specifically binds the polypeptide in an ELISA assay. This assay can be performed either qualitatively or quantitatively. The ELISA assay, as well as other immunological assays for detecting a polypeptide in a sample, are described in *Antibodies: A Laboratory Manual* (1988, Harlow and Lane, eds. Cold Spring Harbor Laboratory, Cold Spring Harbor, N.Y.).

Alternatively, or in addition, the delivery of a biologically active polypeptide can be assessed by testing a sample of blood, plasma, or tissue for an activity associated with the polypeptide (e.g., an enzymatic activity). Where the encoded gene product is delivered to alleviate a condition, disease, or symptom thereof, the efficacy of methods of the invention can be assessed by monitoring the condition of the mammalian subject for improvement. For example, where the polypeptide is the steroid sulphatase (STS) for treatment of X-linked ichthyosis (XLI), the subject's skin can be examined for restoration of epidermal architecture, specifically regeneration of epidermis having normal relative stratum corneum thickness.

Dosage

The amount of DNA to accomplish expression of a desired gene product in skin cells at an effective level (e.g., a level effective to elicit an immune response, to alleviate a symptom of a condition or disease, etc.) will vary according to the desired effect (e.g., immunity, prophylaxis, cosmetic effect, etc.), as well as with other variables such as the age of the subject, the skin cells to be genetically altered, the gene product to be expressed and the desired level of its expression, etc. Because skin's thickness ranges from about 1.5 to 4.0 mm, and exhibits variations due to maturation, ageing, and regional specializations, the ordinarily skilled artisan will appreciate that the dosage may vary accordingly..

In general, the amount of DNA administered is an amount sufficient to provide for transformation of a number of skin cells that in turn provides for a level of gene product expression from the introduced DNA to provide for a desired effect. Dosages are routinely determined in the art, and can be extrapolated from the amounts of DNA effective in an animal mode (e.g., a rodent (mouse or rat) or other mammalian animal model), in which factors such as the efficiency of transformation and the levels of gene product expression achieved can be readily assessed and extrapolated to other vertebrate subjects. Generally speaking, the amount of DNA that is delivered to a human is usually on the order of about 100 times the amount of DNA effective in a rat.

In all of the systemic strategies presented herein, an effective DNA or mRNA dosage will generally be in the range of from about 0.05 μg/kg to about 50 mg/kg, usually about 0.005 to 5 mg/kg. However, as will be appreciated, this dosage will vary in a manner apparent to those of skill in the art according to the activity of the peptide coded for by the DNA or mRNA and the particular peptide used. For delivery of an immunogenic polypeptide to humans, for example, adequate levels of translation are achieved with a DNA or mRNA dosage of about 0.5 to 5 mg/kg.

Regimens for continuing therapy, including dose and frequency may be guided by the initial response and clinical judgment.

EXAMPLES

The following examples are put forth so as to provide those of ordinary skill in the art with a complete disclosure and description of how to carry out the invention and are not intended to limit the scope of what the inventors regard as their invention, nor are they intended to represent or imply that the experiments below are all of or the only experiments performed. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, and temperature is in degrees Centigrade.

Example 1

Topical Delivery of DNA to Skin of Mice and Induction of IgM Antibodies

The ability of DNA:lipid complexes and naked DNA to transfect skin cells following subcutaneous injection or topical application to treated or untreated skin was examined in vivo. The recombinant DNA construct used in this example contained a CMV promoter operably linked to the gene encoding E. coli β-galactosidase (lacZ). A circular form of the construct was used.

Three C57B1 mice were used in each experimental group. The backs of mice were either treated (shaved and then treated with the depilatory Nair™), or untreated prior to DNA administration. DNA:lipid samples were prepared by suspending 100 μg of DNA in a 100 μl volume to provide a solution containing 1:3 DNA:lipofectin (Gibco BRL). Naked DNA samples were prepared by suspending 100 μg in 100 μl of phosphate buffered saline (PBS).

DNA:lipid or naked DNA samples were applied topically or injected subcutaneously onto the treated skin of mice. In addition, naked DNA or DNA:lipid samples were applied topically to untreated skin. Topical application was accomplished by anesthetizing the mice with Avertin, and placing 100 μg DNA in a 100 μl drop on top of the skin for at least 30 minutes. In control group, the same amount of lipofectin was dissolved in 100 μl PBS and likewise applied to the skin. These procedures were repeated at 4, 7, and 10 weeks after the initial administration (boosters). The mice were bled using the retro-orbital technique prior to DNA administration (week 0), as well every week thereafter.

Serum from each timepoint was analyzed for specific anti-β-galactosidase activity by either ELISA assay or western blot according to methods well known in the art. Briefly, ELISA was performed by coating 96 well plates (polystyrene, Costar) with 5 μg/well bacterial β-galactosidase (Sigma) in 20 mM $Na_2CO_3$, pH 9.6, for either 2 hours at room temperature or overnight at 4° C. The plates were then washed three times with TBS-TWEEN 20 (0.02%) for 10 minutes each time. The plates were then blocked with 3% BSA (Sigma) in TBS-TWEEN 20 (0.02%) for 1 hour at room temperature, and the washes repeated. Five microliters of mouse serum was added to each well in the presence of 1% BSA in TBS-TWEEN 20. Two hours later (or after overnight at 4° C.), plates were washed and incubated with alkaline phosphatase-goat anti-mouse IgM (Zymed) for 30 minutes at room temperature to detect mouse IgM antibody bound to the β-galactosidase. p-Nitrophenyl phosphate (pNPP, Sigma) was used as the soluble substrate for the detection of alkaline phosphatase activity associated with the anti-IgM antibody and the plates were read at 410 nm on a microtiter plate reader (Dynatech).

The IgM response of a representative mouse to which naked DNA was topically applied without skin pretreatment is shown in FIG. 1. Topical application of naked DNA without skin pretreatment resulted in antibody kinetics consistent with other response to antigenic challenge. Anti-β-galactosidase IgM was detected in serum as early as one week after topical application of naked DNA to the skin. In addition, this immunization reaction was boosted by re-administration of the naked DNA at weeks 4, 7, and 10, as indicated by the increase in anti-β-galactosidase IgM production following these timepoints. There were no significant differences in the immune responses observed by all other routes tested (namely by subcutaneous injection of DNA, topical application of liposomes to pretreated skin, topical application of liposomes to untreated skin, and application of naked DNA to pretreated skin.)

Skin biopsies were taken from the areas of DNA application to examine whether β-galactosidase expression could be observed in cells following topical application of naked β-galactosidase-encoding DNA. The skin samples were embedded immediately in O.C.T. (Tissue-Tek) and sectioned with a Cryostat (Tissue-Tek), 5 μm/section. The β-galactosidase activity was assayed using X-Gal (Gibco-BRL) staining. Frozen sections were fixed in 2% formaldehyde and 0.2% glutaraldehyde in PBS for 10 mins at room temperature and followed by extensive washing at room temperature with was buffer (0.02% Nonidet P-40, 0.01% deoxycholate and 3% DMSO in PBS, pH 7.2). After washing, the wash buffer was replaced with X-Gal staining solution (wash buffer plus 5 mM potassium ferricyanide, 5 mM potassium ferocyanide, 2 mM $MgCl_2$, 0.01–0.02% X-Gal; the staining solution was filtered (0.45 μm syringe filter, Gelman Science) before adding X-Gal). Skin sections were incubated in the staining solution at 37° C. for 2 to 10 hrs in the dark. After staining, each section was washed with PBS and counterstained with hemotoxylin and eosin (Fisher). The slides were examined under the light microscope (Nikon). However, despite the detection of an anti-β-galactosidase antibody response, no β-galactosidase staining was observed in the skin cells. Similarly, when naked β-galactosidase-encoding DNA was injected subcutaneously into mice having human xenograft, no β-galactosidase staining was detected in the skin. These latter two observations may be due to 1) the transient nature of expression, which may have already subsided to an undetectable level at the time the skin sample was taken; 2) the inability of the X-Gal staining method to detect low levels of expression; and/or 3) the movement of cells expressing β-galactosidase out of the skin prior to taking of the sample.

These results show that, although expression of the introduced polynucleotide was not detectable by staining with X-Gal, topical application of naked polynucleotide successfully resulted in a significant antibody response. These results indicate that genetic immunization can be accomplished by topical administration of naked DNA to skin without skin pretreatment.

Example 2

Anti-β-galactosidase IgG Antibody Titers Following Topical DNA Application

The IgG response in mice immunized as described in Example 1 was examined by ELISA. ELISA was performed as described in Example 1, except that an alkaline phosphatase-goat anti-mouse IgG antibody (Sigma) was used to detect antibodies bound to the β-galactosidase in the ELISA plate. Topical administration of naked DNA resulted in production of anti-β-galactosidase IgG antibodies. Consistent with normal IgG antibody kinetics, production of the anti-β-galactosidase IgG antibodies peaked at about 2–3 weeks after the animal's initial exposure to the antigen.

Figure 2:
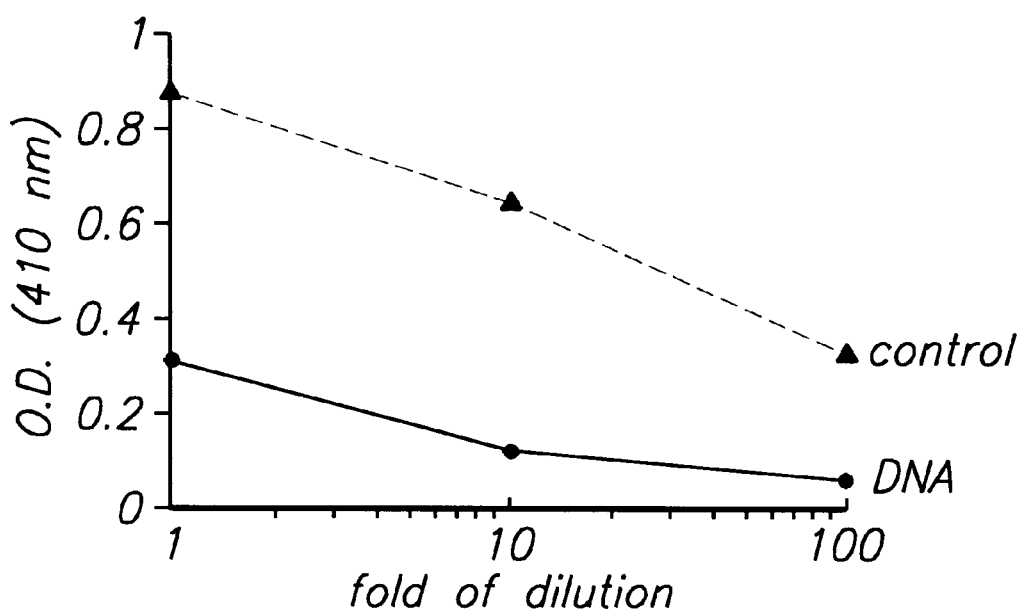
FIG. 2 is a graph showing the titration of binding of immune serum IgG (solid line) and a commercially available anti-β-galactosidase antibody (control, dashed line) to β-galactosidase in an ELISA assay.

In order to assess the specificity of the detected IgG for β-galactosidase, the ability to titrate antibody binding to β-galactosidase was assessed using 10-fold serial dilutions of immune serum in an ELISA. Commercially available rabbit anti-β-galactosidase antibody was used as a positive control (FIG. 2, dotted line). The anti-β-galactosidase IgG antibody from the mice immunized topically with naked DNA was titratable, as shown by the representative titration curve in (FIG. 2, solid line). These data show that the anti-β-galactosidase IgG activity generated by topical immunization, as well as by the other routes tested, is specific for β-galactosidase.

Figure 3:
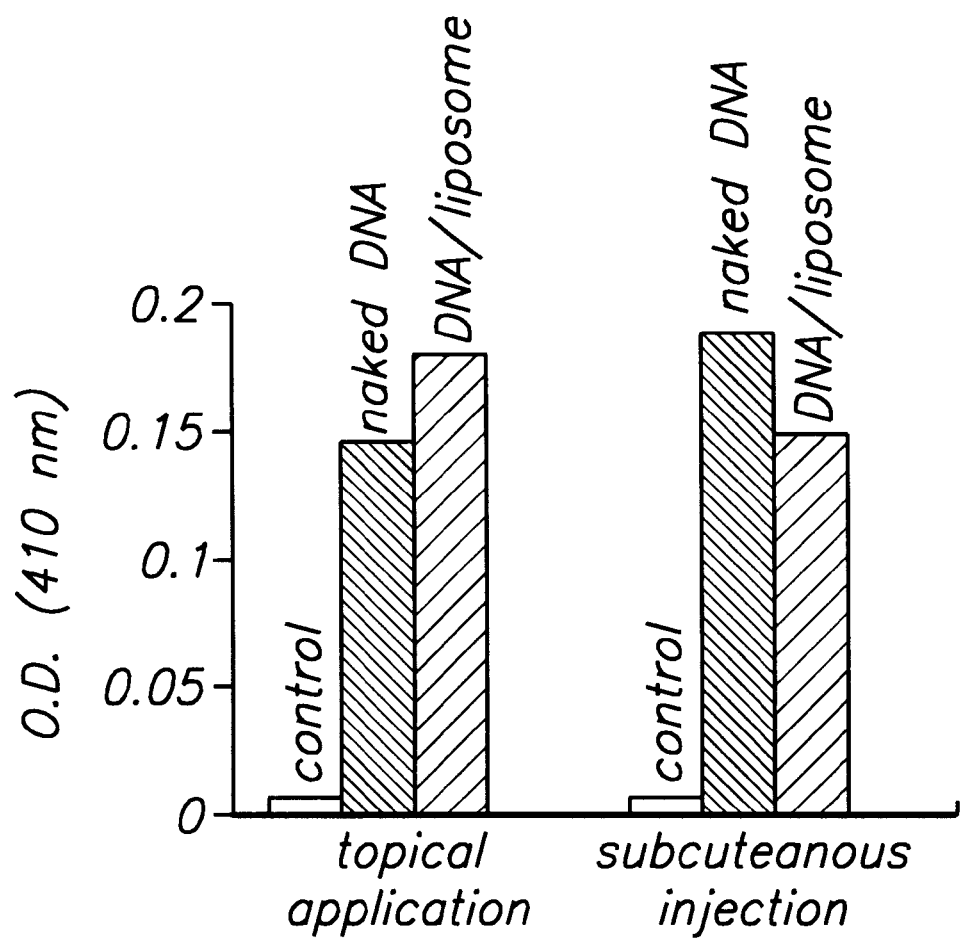
FIG. 3 is a graph showing the relative efficacy of different formulations or delivery routes on IgG production as measured by ELISA.

As determined by ELISA, IgG production was similar for all tested routes of administration and formulations, namely for subcutaneous injection or topical application of lipid-:DNA or naked DNA to pretreated skin (FIG. 3; each bar represents IgG levels of a single animal at 3 weeks post-immunization). Direct intradermal injection of genetic material thus showed no immunizing benefit with respect to the potency of the immune response or the specificity of the antibodies elicited relative to topical delivery of the polynucleotides.

Example 3

Western Blot Analysis of Specificity of Antibodies to β-galactosidase Following Topical Application of β-galactosidase-encoding DNA The specificity of anti-β-galactosidase antibodies produced after topical administration of naked β-galactosidase-encoding DNA to mice was assessed by Western blot. Both preimmune and immune serum were analyzed for their ability to bind to either β-galactosidase or to green fluorescent protein (GFP) in a Western blot performed according to methods well known in the art. Specifically, 10 µg of either bacterial β-galactosidase (Sigma), bovine serum albumin (BSA, control, Sigma), or cell lysates obtained from keratinocytes overexpressing GFP (as a result of transfection with LTR-EGFP) were loaded into a lane of a 10% SDS-PAGE gel. After electrophoresis, the samples were transferred to nitrocellulose membranes. Blots were blocked with 5% dry milk in PBS-TWEEN 20 (0.02%) for 1 hour at room temperature or overnight at 4° C. Blots were then washed three times with PBS-TWEEN 20 (0.02%) for 10 minutes each time, and then incubated with primary antibodies for 1 hour at room temperature.

The blots were then incubated with either preimmune serum, immune serum, rabbit anti-bacterial β-galactosidase (5 Prime→3 Prime, Inc.), mouse anti-GFP (Clontech), or mouse anti-human laminin 5 β-3 subunit, were utilized in order to address the specificity of the immunization. After incubation with the selected antibody, the blots were washed and incubated with secondary antibody for 15 minutes at room temperature (Anti-mouse or rabbit Ig, horseradish peroxidase linked whole antibody, Amersham Life Science). Antibody binding was detected by ECL (Amersham Life Science).

Figure 4A:
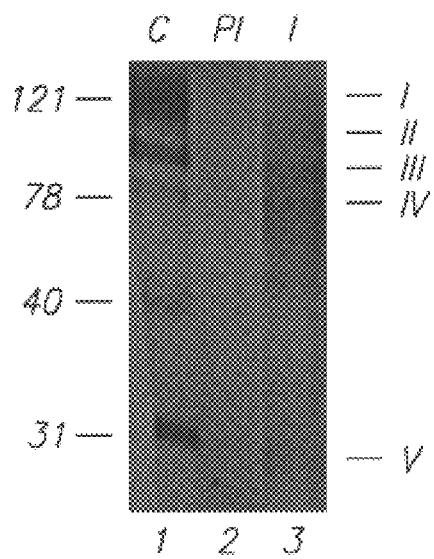
FIGS. 4A–4C show the results of Western analysis to determine the specificity binding of immune and preimmune serum from mice immunized by topical administration β-galactosidase-encoding DNA to β-galactosidase (FIG. 4A), green flourescent protein (GFP.

When blots having purified recombinant bacterial β-galactosidase were incubated with immune serum, the immune serum bound to a protein with molecular weight of 120 kDa, consistent with the molecular weight of β-galactosidase (FIG. 4A, lane 3). This same protein band was bound by the control rabbit anti-β-galactosidase antibody (FIG. 4A, lane 1). In addition to the 120 kDa band, immune serum also bound to four other lower Mr. protein bands (FIG. 4A, lane 3). These bands likely represent β-galactosidase degradation products, since the control rabbit anti-β-galactosidase antibody also bound to these bands (FIG. 4A, lane 1). No binding to β-galactosidase or its degradation fragments was detected when the blot was incubated with preimmune serum (FIG. 4A, lane 2). The antibodies present in immune serum did not bind BSA (data not shown), GFP (FIG. 4B, lane 2), or laminin 5 (FIG. 4C, lane 1), even when these proteins were the only (in the case of BSA) or the most abundant proteins (in the case of GFP and laminin) on the blots. These data show that the immune serum from mice immunized by topical application of β-galactosidase-encoding DNA specifically bind to β-galactosidase.

Example 4

Competition Binding Assays to Determine the Specificity of Antibodies to β-galactosidase Following Topical Application of β-galactosidase-encoding DNA In order to further assess the specification of immune sera from mice immunized with β-galactosidase-encoding DNA by topical administration the ability of immune serum to compete for binding with β-galactosidase was analyzed. To this end, 10-fold serial dilutions of β-galactosidase (10 µg, 1 µg, 0.1 µg, and 0.01 µg respectively) were either loaded onto an SDS-PAGE gel or spotted in duplicates onto a nitrocellulose membrane. SDS-PAGE gels were processed as described in Example 3. The resulting blots were then incubated with either preimmune serum or immune serum. Rabbit-anti-β-galactosidase antibody (positive control).

Figure 4B:
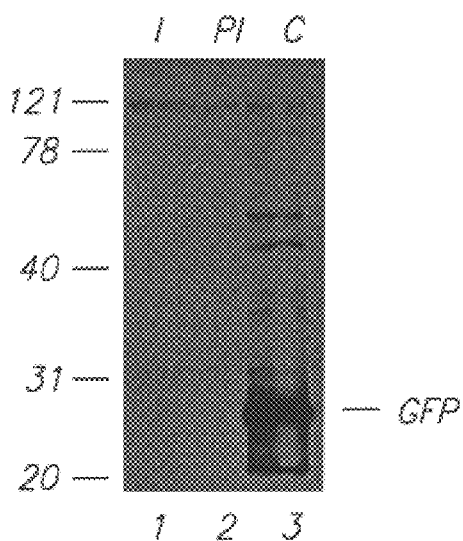
Figure 4C:
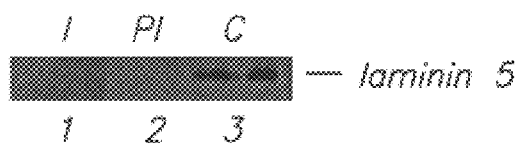
Figure 5A:
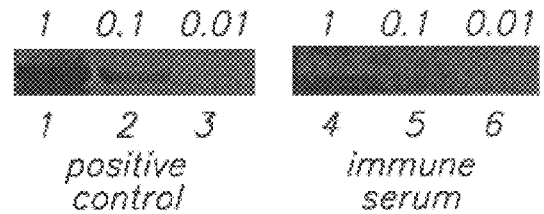
FIGS. 5A–5B show the results of Western analysis to determine the potency of anti-β-galactosidase antibodies of immune serum of mice immunized by topical administration of β-galactosidase-encoding DNA.
Figure 5B:
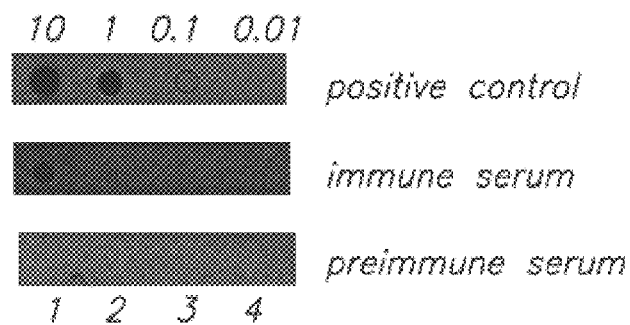

The antibody activity is totally dependent on the available binding sites (FIGS. 4A and 4B). In total, these findings indicate that topical DNA plasmid vectors applied to the mouse skin induce specific antibody immunity.

Following procedures similar to those described above, other gene products can be expressed from DNA inserted into a skin cell by a method of the invention.

The invention now being fully described, it will be apparent to one of ordinary skill in the art that many changes and modifications can be made thereto without departing from the spirit or scope of the appended claims.

What is claimed is:

1. A method for inducing an immune response in a vertebrate, the method comprising the steps of:

applying topically to skin of a subject an immunogen-encoding polynucleotide in an amount sufficient for uptake by a skin cell and sufficient for expression of the immunogen-encoding polynucleotide and induction of an immune response, wherein the skin to which the polynucleotide is applied comprises hair and is not treated with a chemical or mechanical irritant, and wherein the polynucleotide is operably linked to a promoter, and is not contained within a viral particle.

2. The method of claim 1, wherein the skin to which the polynucleotide is applied is intact.

3. The method of claim 1, wherein the polynucleotide is free of calcium phosphate.

4. The method of claim 1, wherein the subject is a mammal.

5. The method of claim 1, wherein the subject is a human.

6. The method of claim 1, wherein the immunogen-encoding polynucleotide is a polynucleotide encoding a polypeptide selected from the group consisting of a viral polypeptide, a bacterial polypeptide, and a polypeptide of a parasite.

7. A method for inducing an immune response in a vertebrate, the method comprising the steps of:

applying topically to skin of a subject an immunogen-encoding polynucleotide in an amount sufficient for uptake by a skin cell and sufficient for expression of the immunogen-encoding polynucleotide and induction of an immune response, wherein hair is not removed from the skin prior to applying the polynucleotide and the skin is not treated with a chemical or mechanical irritant, and wherein the polynucleotide is operably linked to a promoter and is not contained within a viral particle.

8. A method for introducing a polynucleotide into a skin cell in vivo for expression of a gene product encoded by the introduced polynucleotide, the method comprising the steps of:

applying topically to skin of a subject a polynucleotide in an amount sufficient for uptake by a skin cell and sufficient for expression of a gene product encoded by the polynucleotide to provide in the subject a biological effect associated with gene product expression; wherein the skin to which the polynucleotide is applied comprises hair and is not treated with a chemical or mechanical irritant, and wherein the polynucleotide is operably linked to a promoter, and is not contained within a viral particle.

9. The method of claim 8, wherein the skin to which the polynucleotide is applied is intact.

10. A method for delivering a polypeptide to a subject, the method comprising the steps of:

applying topically to skin of a subject a polypeptide-encoding polynucleotide in an amount sufficient for uptake by a skin cell and sufficient for expression of the polypeptide to provide in the subject a biological effect associated with polypeptide expression; wherein the skin to which the polynucleotide is applied comprises hair and is not treated with a chemical or mechanical irritant, and wherein the polynucleotide is operably linked to a promoter, and is not contained within a viral particle.

11. The method of claim 1, wherein the polynucleotide is administered in the absence of an amount of liposomes or charged lipids effective to facilitate transfection.

12. The method of claim 1, wherein the skin is epidermis.

13. The method of claim 7, wherein the skin is epidermis.

14. The method of claim 8, wherein the skin is epidermis.

15. The method of claim 10, wherein the polynucleotide is administered in the absence of an amount of liposomes or charged lipids effective to facilitate transfection.

* * * * *